(12) United States Patent
Tezel et al.

(10) Patent No.: US 12,194,053 B2
(45) Date of Patent: *Jan. 14, 2025

(54) COMPOSITIONS AND METHODS FOR REDUCING OXIDATIVE DAMAGE

(71) Applicant: University of Louisville Research Foundation, Inc., Louisville, KY (US)

(72) Inventors: Tongalp H. Tezel, New York, NY (US); Andrea S. Gobin, Pearland, TX (US); Martin G. O'Toole, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/204,225

(22) Filed: May 31, 2023

(65) Prior Publication Data

US 2024/0041907 A1 Feb. 8, 2024

Related U.S. Application Data

(60) Continuation of application No. 17/356,082, filed on Jun. 23, 2021, now Pat. No. 11,701,375, which is a continuation of application No. 16/227,680, filed on Dec. 20, 2018, now abandoned, which is a continuation of application No. 15/385,416, filed on Dec. 20, 2016, now Pat. No. 10,195,225, which is a division of application No. 14/646,660, filed as application No. PCT/US2013/071319 on Nov. 21, 2013, now Pat. No. 9,555,054.

(60) Provisional application No. 61/728,900, filed on Nov. 21, 2012.

(51) Int. Cl.
| | |
|---|---|
| C08F 2/46 | (2006.01) |
| A61K 9/00 | (2006.01) |
| A61K 31/7016 | (2006.01) |
| A61K 47/32 | (2006.01) |
| A61K 47/38 | (2006.01) |
| C08F 2/50 | (2006.01) |
| C08G 61/04 | (2006.01) |
| C08L 1/28 | (2006.01) |
| C08L 5/02 | (2006.01) |
| C08L 5/08 | (2006.01) |
| C08L 5/10 | (2006.01) |
| C08L 33/14 | (2006.01) |
| A61F 9/00 | (2006.01) |

(52) U.S. Cl.
CPC ........ *A61K 31/7016* (2013.01); *A61K 9/0048* (2013.01); *A61K 9/0051* (2013.01); *A61K 47/32* (2013.01); *A61K 47/38* (2013.01); *C08L 1/284* (2013.01); *C08L 5/02* (2013.01); *C08L 5/08* (2013.01); *C08L 5/10* (2013.01); *C08L 33/14* (2013.01); *A61F 9/00* (2013.01); *C08L 2205/05* (2013.01)

(58) Field of Classification Search
CPC ...... C08L 5/08; C08L 5/02; C08L 5/10; C08L 33/14; C08L 1/284; C08L 71/02; C08L 2205/05; A61P 39/06; A61P 27/02; A61K 31/706; A61K 9/0048; A61K 9/0051; A61K 47/38; A61K 47/22; A61F 9/00
USPC ................. 522/63, 6, 189, 184, 71, 1; 520/1
See application file for complete search history.

(56) References Cited

U.S. PATENT DOCUMENTS

| | | |
|---|---|---|
| 4,778,815 A | 10/1988 | Cash |
| 5,422,376 A | 6/1995 | Webb |
| 5,626,863 A | 5/1997 | Hubbell |
| 5,767,105 A | 6/1998 | Peyman |
| 5,785,993 A | 7/1998 | Baker et al. |
| 5,801,033 A | 9/1998 | Hubbell |
| 5,804,597 A | 9/1998 | Yamakoshi |
| 5,876,438 A | 3/1999 | Kelleher |
| 6,060,582 A | 5/2000 | Hubbell |
| 6,121,341 A | 9/2000 | Sawhney |
| 6,149,931 A | 11/2000 | Schwartz |
| 6,306,922 B1 | 10/2001 | Hubbell |

(Continued)

FOREIGN PATENT DOCUMENTS

| | | | |
|---|---|---|---|
| CN | 101401791 | | 4/2009 |
| EP | 1192947 | | 4/2002 |
| EP | 1782795 | | 5/2007 |
| JP | H09235233 | | 9/1997 |
| JP | 2005104970 | * | 4/2005 |
| JP | 2005104970 A | * | 4/2005 |

(Continued)

OTHER PUBLICATIONS

Kiyobayashi, JP 2005-104970 Machine Translation, Apr. 21, 2005 (Year: 2005).*

(Continued)

*Primary Examiner* — Jessica Whiteley
(74) *Attorney, Agent, or Firm* — Khin K. Chin; Bozicevic, Field & Francis LLP

(57) ABSTRACT

Polymeric compositions are provided that include a poly (ethylene glycol), a viscoelastic polymer, and an antioxidant, where, in polymerized form, the compositions have a refractive index of about 1.30 to about 1.40. Methods of synthesizing the compositions are also provided and include the steps of heating an amount of water, adding a buffering agent to the water to form a buffer solution; mixing a poly (ethylene glycol) and a viscoelastic polymer into the buffer solution to form a reactive mixture; adding a plurality of antioxidant particles to the reactive mixture; and removing suspended gas bubbles from the reactive mixture. Methods of preventing oxidative damage to an eye lens of a subject are further provided and include administering the foregoing polymeric compositions to the eye lens of the subject.

14 Claims, 7 Drawing Sheets

(56) References Cited

U.S. PATENT DOCUMENTS

| | | | |
|---|---|---|---|
| 6,387,977 | B1 | 5/2002 | Sawhney |
| 6,399,655 | B1 | 6/2002 | De Juan |
| 6,433,007 | B1 | 8/2002 | Gamer et al. |
| 6,475,508 | B1 | 11/2002 | Schwartz |
| 6,555,526 | B2 | 4/2003 | Matsuo |
| 6,602,975 | B2 | 8/2003 | Hubbell |
| 6,635,267 | B1 * | 10/2003 | Miyoshi ............ A61P 19/02 424/78.17 |
| 6,780,427 | B2 | 8/2004 | Baker et al. |
| 7,238,364 | B2 | 7/2007 | Sawhney |
| 7,589,107 | B2 | 9/2009 | Matier |
| 7,727,544 | B2 | 6/2010 | Schwartz |
| 7,732,425 | B2 | 6/2010 | Matsuo |
| 7,906,136 | B2 | 3/2011 | Wong |
| 7,976,833 | B2 | 7/2011 | Soli |
| 8,389,014 | B2 | 3/2013 | Longo |
| 8,741,871 | B2 | 6/2014 | Nishizawa |
| 8,784,897 | B2 | 7/2014 | Archambeau |
| 8,962,684 | B2 | 2/2015 | Tojo et al. |
| 2002/0192289 | A1 | 12/2002 | Zheng et al. |
| 2003/0087985 | A1 | 5/2003 | Hubbell |
| 2003/0223957 | A1 | 12/2003 | Schwartz |
| 2004/0033274 | A1 | 2/2004 | Hong |
| 2004/0086479 | A1 | 5/2004 | Grinstaff |
| 2004/0131582 | A1 | 7/2004 | Grinstaff |
| 2004/0138329 | A1 | 7/2004 | Hubbell |
| 2004/0229814 | A1 | 11/2004 | Dillon |
| 2005/0271590 | A1 | 12/2005 | Schwartz |
| 2006/0052340 | A1 | 3/2006 | Tsuzuki |
| 2006/0057215 | A1 | 3/2006 | Raiche |
| 2006/0257391 | A1 | 11/2006 | Bartels |
| 2008/0008698 | A1 | 1/2008 | Bartels |
| 2008/0132444 | A1 | 6/2008 | Li et al. |
| 2009/0048188 | A1 | 2/2009 | Matsuo |
| 2009/0170789 | A1 | 7/2009 | Gitlin |
| 2010/0297193 | A1 | 11/2010 | Archambeau |
| 2011/0033540 | A1 | 2/2011 | Daniloff |
| 2011/0054441 | A1 | 3/2011 | Erickson |
| 2011/0136935 | A1 | 6/2011 | Khor et al. |
| 2011/0166247 | A1 | 7/2011 | Myung et al. |
| 2011/0182968 | A1 | 7/2011 | Myung et al. |
| 2011/0243883 | A1 | 10/2011 | Grinstaff |
| 2012/0082730 | A1 | 4/2012 | Banerjee |
| 2012/0189667 | A1 | 7/2012 | Boutros |
| 2013/0317457 | A1 | 11/2013 | Schmitt |
| 2013/0331458 | A1 | 12/2013 | Miyano et al. |
| 2014/0018316 | A1 | 1/2014 | Matsuo |
| 2014/0031542 | A1 | 1/2014 | Chen |
| 2014/0099375 | A1 | 4/2014 | Archambeau |
| 2014/0377838 | A1 | 12/2014 | Maynard et al. |
| 2015/0010634 | A1 | 1/2015 | Knappe et al. |
| 2015/0290230 | A1 | 10/2015 | Tezel et al. |
| 2018/0153917 | A1 | 6/2018 | Tezel |

FOREIGN PATENT DOCUMENTS

| | | |
|---|---|---|
| WO | WO 198700196 | 1/1987 |
| WO | WO 199317669 | 9/1993 |
| WO | WO 199724129 | 7/1997 |
| WO | WO 2000037066 | 6/2000 |
| WO | WO 2003080091 | 10/2003 |
| WO | WO 2004050795 | 6/2004 |
| WO | WO 2005048920 | 6/2005 |
| WO | WO 2011135400 | 11/2011 |
| WO | WO 2013046059 | 4/2013 |
| WO | WO 2014066658 | 5/2014 |
| WO | WO 2014081969 | 5/2014 |

OTHER PUBLICATIONS

Abdelkader, H., et al., (2014) "Age-related cataract and drug therapy: opportunities and challenges for topical antioxidant delivery to the lens"; Journal of Pharmacy and Pharmacology,.67(4): p. 537-550.

Aragona, P., et al. (2014) "Protective effects of trehalose on the corneal epithelial cells"; , Scientific WorldJournal 2014:717835. doi: 10.1155/2015/717835.

Attanasio, F., et al., (2007) "Trehalose effects on a-crystallin aggregates"; Biochemical and Biophysical Research Communications, 354: p. 899-905.

Ayranci, E., et al. (2003) "A Method for the Measurement of the Oxygen Permeability and the Development of Edible Films to Reduce the Rate of Oxidative Reactions in Fresh Foods"; Food Chemistry, 80(3): p. 423-43.

Barbazetto, I.A., et al. (200) "4Oxygen Tension in the Rabbit Lens and Vitreous before and after Vitrectomy"; Exp Eye Res, 78(5): p. 917-924.

Bator, A., et al., (2014) "Trehalose-Based Eye Drops Preserve Viability and Functionality of Cultured Human Corneal Epithelial Cells during Desiccation"; Biomedical Research International 2014(3): 8 pages.

Baudouin, C., et al., Role of hyperosmolarity in the pathogenesis and management of dry eye disease: proceedings of the Ocean group meeting, Ocul Surf. Oct. 2013;11(4):246-58. doi: 10.1016/j.tos.2013.07.003.

Beebe, D.C., et al. (2010) "Oxidative Damage and the Prevention of Age-Related Cataracts"; Ophthalmic Res, 44(3): p. 155-165.

Beebe, D.C., et al. (2011) "VitreoretinalInfluences on Lens Function and Cataract"; Philos Trans R Soc Lond B Bioi Sci, 366 1568): p. 1293-300.

Buerk, D.G., et al. (1993) "02 Gradients and Countercurrent Exchange in the Cat Vitreous Humor near Retinal Arterioles and Venules"; Microvasc Res, 45(2): p. 134-148.

Buwalda, S.J., et al. (2011) "Self-Assembly and Photo-Cross-Linking of Eight-Armed Peg-Ptmc Star Block Copolymers"; Biomacromolecules, 12(7): p. 2746-2754.

Cai, M., et al. (2014) "Mitochondria-Targeted Antioxidant Peptide SS31 Protects Cultured Human Lens Epithelial Cells against Oxidative Stress"; Current Eye Research: p. 1-8.

Cao, S., et al., (2014) Prevention of Selenite-Induced Cataratogenesis by Ginkgo biloba Extract (Egb761) in Wistar Rats; Current Eye Research; p. 1-6.

Cejkova, J. (2010) "Reduced UVB-induced corneal damage caused by reactive oxygen and nitrogen species and ecreased changes in corneal optics after trehalose treatment"; Histol. Histopathol., 25: p. 1403-1416.

Cejkova, J. (2011) "Favorable effects of trehalose on the development of UVB-mediated antioxidant/pro-oxidant imbalance in the corneal epithelium, proinflammatory cytokine and matric metalloproteinase induction, and heat shock protein 70 expression"; GraefesArch. Clin. Exp. Ophthalmol., 249: p. 1185-1194.

Charles, P.T., et al. (2009) "Reduction of Non-Specific Protein Adsorption Using Poly(Ethylene) Glycol (Peg) Modified Polyacrylate Hydrogels in Immunoassays for Staphylococcal Enterotoxin B Detection"; Sensors, 9(1): p. 645-55.

Chen, M., (2014) "Epigallocatechin gallate eye drops protect against ultraviolet B-induced corneal oxidative damage in mice"; Molecular Vision,20: p. 153-162.

Chen, W., et al., (2009) "Trehalose protects against ocular surface disorders in experimental murine dry eye through suppression of apoptosis"; Exp Eye Res 89: p. 311-318.

De Moura, M.R., et al. (2008) "Properties of Novel Hydroxypropyl Methylcellulose Films Containing Chitosan Nanoparticles"; Journal of food science, 73(7): p. N31-7.

Emanuele, E., et al., (2014) "Protective effect of trehalose-loaded liposomes against UVB-induced photodamage in human keratinocytes"; Biomedical Reports 2: p. 755-759.

European Patent Office, Extended European Search Report issued in corresponding Application No. EP 13 85 463, mailed Jun. 8, 2016.

Geraldine, P., et al. (2006) "Prevention of Selenite-Induced Cataractogenesis by Acetyi-L-Carnitine: An Experimental Study"; Exp Eye Res, 83(6): p. 1340-9.

(56) References Cited

OTHER PUBLICATIONS

Grama, C., et al., Efficacy of Biodegradable Curcumin Nanoparticles in Delaying Cataract in Diabetic Rat Model, PLos One 8(10):e78217. doi: 10.1371/journal.pone.0078217.
Gross, N., et al., Choroidal neovascularization reduced by targeted drug delivery with cationic liposome-encapsulated paclitaxel or targeted photodynamic therapy with verteporfin encapsulated in cationic liposomes, Mol Vos. 2013; 19:54-61.
Hammond, B., et al., Oxidative photodegradation of ocular tissues: Beneficial effects of filtering and exogenous ntioxidants, Experimental Eye Research 2014, 129:135-150.
Hayashi, K., et al., (2004) "Posterior capsule opacification after implantation of a hydrogel intraocular lens"; Br J Ophthalmol ;88(2): p. 182-185.
He, Q., et al., "Trehalose alleviates PC12 neuronal death mediated by lipopolysaccharide-stimulated BV02 cells via inhibiting nuclear transcription factor NF-KB and AP-1 activation"; Neurotox Res. Nov. 2014;26(4):430-9.
Hermans, K., et al., Cytotoxicity and anti-inflammatory activity of cyclosporine A loaded PLGA nanoparticles for Ocular use, Pharmazie Jan. 2014;69(1):32-7.
Hill-Bator, A., et al. (2014) "Trehalose-based eye drops preserve viability and functionality of cultured human corneal epithelial cells during desiccation"; Biomed Res Int; 2014:292138. doi: 10.1155/2014/292139.
Hillel, A.T., et al. (2011) "Photoactivated Composite Biomaterial for Soli Tissue Restoration in Rodents and in Humans"; Science translational medicine, 3(93): p. 93ra67.
Hill-West, J.L., et al. (1994) "Inhibition of Thrombosis and Intimal Thickening by in Situ Photopolymerization of Thin Hydrogel Barriers"; Proceedings of the National Academy of Sciences of the United States of America, 91 (13): p. 5967-71.
Holekamp, N.M., et al. (2005) "Vitrectomy Surgery Increases Oxygen Exposure to the Lens: A Possible Mechanism for Nuclear Cataract Formation"; Am J Ophthalmol, 139(2): p. 302-310.
Hovakimyan, M., et al., (2012) "Evaluation of Protective Effects of Trehalose on Desiccation of Epithelial Cells in Three Dimensional Reconstructed Human Corneal Epithelium"; Current Eye Research, 37(11 ):p. 982-989.
Islam, MN, et al. (2011) "Eye Diseases-Treatment and Prevention with Antioxidants"; Medicine Today, vol. 23, No. 02, pp. 103-105.
Johnson, L.M., et al. (2010) "Formation of three-dimensional hydrogel multilayers using enzyme-mediated redox chain eaction initiation"; ACS Appl Mater Interfaces, 2(7): 1963-72.
Kan, E., et al., Effects of two antioxidants; a-lipoic acid and fisetin against diabetic cataract in mice, Int. Ophthalmol 015 35:115-120.
Kawata, T., et al., (2014) "Glass transition temperature of dried lens tissue pretreated with trehalose, maltose, or cyclic etrasaccharide"; SpringerPius, 3: p. 317.
Kleinberg, T.T., et al. (2011) "Vitreous Substitutes: A Comprehensive Review"; Surv Ophthalmol, 56(4): p. 300-23.
Li J., et al., Therapeutic efficacy of trehalose eye drops for treatment of murine dry eye induced by an intelligently controlled environmental system, Mol Vis 2012; 18:317-29.
Lin, S., et al. (2011) "Influence of physical properties of biomaterials on cellular behavior"; Pharm Res., 28(6): 1422-30.
Luo, Y., et al., (2008) "Trehalose: Protector of antioxidant enzymes or reactive oxygen species scavenger under heat stress?"; Environmental and Experimental Botany, 63: p. 378-384.
Luyckx, J., et al., (2011) "Trehalose: an intriguing disaccharide with potential for medical application in ophthalmology"; Clinical Ophthalmology: 5: p. 577-581.
Mann, B.K., et al. (2001) "Smooth Muscle Cell Growth in Photopolymerized Hydrogels with Cell Adhesive and Proteolytically Degradable Domains"; Synthetic Ecm Analogs for Tissue Engineering. Biomaterials, 22(22): p. 3045-3051.
Matsuo, T., et al. (2002) Trehalose Eye Drops in the Treatment of Dry Eye Syndrome, Ophthalmology, 109(11): p. 2024-2029.
Matsuo, T., et al., (2004) "Trehalose Versus Hyaluronan or Cellulose in Eyedrops for the Treatment of Dry Eye"; Jpn. J. Ophthalmol., j48: p. 321-327.
Nakamura, T., (2008) "The use of trehalose-treated freeze-dried amniotic membrane for ocular surface reconstruction"; Biomaterials, 29: p. 3729-3737.
Ouasti, S., et al. (2011) "Network Connectivity, Mechanical Properties and Cell Adhesion for Hyaluronic Acid/Peg Hydrogels"; Biomaterials, 32(27): p. 6456-70.
Park, Y.D., et al. (2003) "Photopolymerized Hyaluronic Acid-Based Hydrogels and Interpenetrating Networks"; Biomaterials, 24(6): p. 893-900.
Pekel, N., (2004) "Radiation Crosslinking of Biodegradable Hydroxypropylmethylcellulose"; Carbohydrate Polymers, 55(2): p. 139-147.
Porter, A.M., et al. (2011) "Biomimetic Hydrogels with VEGF Induce Angiogenic Processes in Both Huvec and Hmec"; Biomacromolecules, 12(1): p. 242-246.
Priya, R., et al. (2014) "Virulence, Speciation and Antibiotic Susceptibility of Ocular Coagualase Negative Staphylococci (CoNS)"; J Clin Diagn Res,;8(5): DC33-7. doi: 10.7860/JCDR/2014/7867.4395.
Sabnis, A., et al. (2009) "Cytocompatibility Studies of an in Situ Photopolymerized Thermoresponsive Hydrogel Nanoparticle System Using Human Aortic Smooth Muscle Cells"; Journal of biomedical materials research. Part A, 91(1): p. 52-59.
Sheu, S., et al., "Resveratrol Stimulates Mitochondrial Bioenergetics to Protect Retinal Pigment Epithelial Cells from Oxidative Damage"; IOVS 2013, 54(9): 6426-6438.
Shin, S.C., et al. (2003) "Preparation and Evaluation of Bioadhesive Benzocaine Gels for Enhanced Local Anesthetic Effects"; International journal of pharmaceutics, 260(1): p. 77-81.
Shui, Y.B., et al. (2006) "Oxygen Distribution in the Rabbit Eye and Oxygen Consumption by the Lens"; Invest Ophthalmol Vis Sci, 47(4): p. 1571-180.
State Intellectual Property Office of China (SIPO), First Office Action issued in corresponding Application No. 201380071008.0, mailed Jun. 24, 2016.
Stefansson, E., (2009) "Physiology of Vitreous Surgery"; Graefes Arch Clin Exp Ophthalmol, 247(2): p. 147-163.
Sunkireddy, P., et al., "Natural antioxidant biomolecules promises future nanomedicine based therapy for cataract"; Colloids and Surfaces B: Biointerfaces 2013 112:554-562.
Takeuchi, K., et al., Inhibitory effects of trehalose on fibroblast proliferation and implications for ocular surgery, Exp Eye Res. Nov. 2010;91(5):567-77. doi: 10.1016/j.exer.2010.07.002.
Thassu et al.; "Ocular Drug Delivery Systems: Barriers and Application of Nanoparticulate Systems"; Oct. 2, 2012, CRC Press, p. 404.
Wang, Y.X., et al. Effects of the Chemical Structure and the Surface Properties of Polymeric Biomaterials on Their Biocompatibility. Pharmaceutical Research, 21(8): p. 1362-1373, 2004.
Wieland, et al., (2007) "Non-viral vector delivery from PEG-hyaluronic acid hydrogels"; Journal of Controlled Release 120(3): p. 233-41.
Wikstrom, J., et al., Viability of freeze dried microencapsulated human retinal pigment epithelial cells, Eur J Pharm Sco, Sep. 29, 2012;47(2):520-6. doi: 10.1016/j.ejps.2012.06.014.
Williams, C.G., et al. (2005) "Variable Cytocompatibility of Six Cell Lines with Photoinitiators Used for Polymerizing Hydrogels and Cell Encapsulation"; Biomaterials, 26(11): p. 1211-1218.
"Frequently asked questions about how science works"; Understanding Science How Science Really Work; downloaded online on May 16, 2021. (Year: 2012) https://undsci.berkeley.edu/faqs.php.
European Patent Office, First Examination Report issued in corresponding Application No. EP16749665, mailed Feb. 28, 2020.
European Patent Office, Supplementary European Search Report issued in corresponding Application No. EP16749665, mailed Oct. 23, 2018.
International Search Report issued in corresponding Application No. PCT/US2016/017005, mailed Apr. 19, 2016.
Hyperphysics, http://hyperphysics.phy-astr.gsu.edu/hbase/vision/eyescal.html, 2000 (Year: 2000).

(56) References Cited

OTHER PUBLICATIONS

Liesegang, Thomas (1990) "Viscoelastic Substances in Ophthalmology" *Survey of Ophthalmology* 34(4):268-293.
Matsuo, T. (2005) "Cyclic Tetrasaccharide Delays Cataract Formation in the Lens in Vitro," Cell Preservation Technology 3(4):238-243.
Yasui, T., et al. (2011) "Characterization of Low Viscosity Polymer Solutions for Microchip Electrophoresis of Non-Denatured Proteins on Plastic Chips"; Biomicrofluidics, 5(4).

\* cited by examiner

Day 0    Day 1    Day 2    Day 6

1mM - Day 1    1mM - Day 5

0.5mM/Day 1   0.5mM/Day 6   0.5mM/Day 11   0.5mM/Day 14   0.5mM/Day 18

Day 2                    Day 8

COMPOSITIONS AND METHODS FOR REDUCING OXIDATIVE DAMAGE

RELATED APPLICATIONS

This application is a continuation application of U.S. application Ser. No. 17/356,082, filed Jun. 23, 2021 now U.S. Pat. No. 11,701,375 which is continuation application of U.S. application Ser. No. 16/227,680, filed Dec. 20, 2018, now abandoned which is a continuation application of U.S. application Ser. No. 15/385,416, filed Dec. 20, 2016, now U.S. Pat. No. 10,195,225 which is a divisional application of U.S. application Ser. No. 14/646,660, filed May 21, 2015, now U.S. Pat. No. 9,555,054 which is a 35 U.S.C. § 371 National Stage Application of International Application No. PCT/US2013/071319, filed Nov. 21, 2013, which claims priority from U.S. Provisional Application Ser. No. 61/728,900, filed Nov. 21, 2012, the entire disclosure of which is incorporated herein by this reference.

TECHNICAL FIELD

The presently-disclosed subject matter relates to compositions and methods for reducing oxidative damage. In particular, the presently-disclosed subject matter relates to compositions and methods for reducing oxidative damage that make use of a combination of polymeric materials and an antioxidant for protecting an eye lens from oxidative damage.

BACKGROUND

The lens of the eye is a biconvex transparent structure that helps to focus light onto the retina, where mature fiber cells of the lens contain high amounts of protein and are important for the transparency and refractive power of the lens. Normally, these proteins are protected from oxidation by reducing substances and by the low-oxygen environment around the lens. Indeed, within the eye, oxygen concentration decreases sharply from the retina towards the lens due to the presence of the vitreous gel. As such, surgical removal or involutional degeneration of the vitreous gel often increases the exposure of the lens to oxygen originating from the retinal vasculature.

Vitrectomy is the surgical method used to remove some or all of the vitreous gel from the eye. It is an essential step of many vitreoretinal surgical procedures and is performed on approximately 500,000 patients per year in the United States alone. However, removal of the vitreous often results in an efflux of oxygen inside the eye through diffusion from the retina-choroid complex and/or ion-assisted transport of oxygen through the vitreous gel. In addition, oxygen is also introduced through the surgical incisions and gases or solutions used to temporarily replace the vitreous gel. As a result, nearly half of patients develop secondary cataracts within two years after undergoing a vitrectomy due to increased intraocular oxygen levels.

Current practices after vitrectomy to reduce the risk of cataract formation include requiring patients to maintain tedious head-down positions to keep the gas bubbles away from the lens until the bubbles are completely absorbed. Unfortunately, maintaining a head-down position for a prolonged time is often highly challenging, especially among the elderly, and may have several side-effects, such as ulnar nerve pinching. Thus, half of the patients facing these requirements after vitrectomy are ultimately not compliant. Nevertheless, there is currently no other medical or surgical method effective to prevent the onset of post-vitrectomy cataracts.

Accordingly, there remains a need for a composition and/or method that can maintain low oxygen pressure around the eye lens to prevent oxidative damage and the formation of lens opacities, but that is also biocompatible, does not require invasive surgery, and does not unduly compromise a subject's vision.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes compositions and methods for reducing oxidative damage. In particular, the presently-disclosed subject matter includes compositions and methods for reducing oxidative damage that make use of a combination of polymeric materials and an antioxidant for protecting an eye lens from oxidative damage.

In some embodiments of the presently-disclosed subject matter, a polymeric composition is provided that comprises a poly(ethylene glycol), a viscoelastic polymer, and an antioxidant, where, in polymerized form, the composition has a refractive index of about 1.30 to about 1.40 to allow the polymeric composition to be effectively used in the eye lens of a subject. In some embodiments, the refractive index of the compositions is about 1.33 to about 1.36.

The poly(ethylene glycol) included in the compositions described herein can, in some embodiments, vary depending on the intended use of the composition and can include poly(ethylene glycol) alone or can include poly(ethylene glycol) linked to other functional moieties that assist in the assembly of the polymeric composition. For example, in some embodiments, the poly(ethylene glycol) included in the compositions is poly(ethylene glycol) diacrylate. In some embodiments, the poly(ethylene glycol) has a molecular weight of about 2000 Da to about 20000 Da and, in some embodiments, is included in the composition at a concentration of about 50 mg/mL to about 150 mg/mL.

With regard to the viscoelastic polymers included in the compositions, in some embodiments, the viscoelastic polymer is selected from the group consisting of hyaluronic acid or a salt thereof, hydroxymethylpropyl cellulose, chondroitin sulfate, polyacrylamide, collagen, dextran, heparin, agarose, chitosan, and a combination thereof. In some particular embodiments, the viscoelastic polymer is hyaluronic acid or a salt thereof, and the hyaluronic acid or the salt thereof is included in the composition at a concentration of about 8 mg/mL to about 12 mg/mL. In other embodiments, the viscoelastic polymer is hydroxymethylpropyl cellulose, and the hydroxymethylpropyl cellulose is included in the composition at a concentration of about 1 mg/mL to about 40 mg/mL In some embodiments, the hydroxymethylpropyl cellulose has a viscosity of about 200 cP to about 5600 cP at 2% concentration in water at 20° C., and, in some embodiments, the hydroxymethylpropyl cellulose has a molecular weight of about 200,000 Da. Further, in some embodiments, the hydroxymethylpropyl cellulose included in the compositions can vary depending on the intended use of the composition and can include hydroxymethylpropyl cellulose linked to other functional moieties that assist in the assembly of the polymeric compositions. For instance, in some embodiments, the hydroxymethylpropyl cellulose included in the compositions is hydroxymethylpropyl cellulose acrylate.

Regardless of the particular visco-elastic polymer and poly(ethylene glycol) materials included in a composition of the presently-disclosed subject matter, once combined and polymerized, the poly(ethylene glycol) and the viscoelastic polymer generally take the form of an inter-penetrating polymer, a cross-linked polymer, or a combination thereof. In some embodiments, to tune the properties of the compositions and provide a composition that can effectively be utilized in the eye and, more specifically, with the eye lens of a subject, the poly(ethylene) glycol and the viscoelastic polymer are included in the composition at a ratio of poly(ethylene glycol) to viscoelastic polymer of about 5:3, about 5:2, about 5:1, about 6:1, about 7:1, about 8:1, about 9:1, about 10:1, about 11.1, about 12:1, about 13:1, about 14:1, about 15:1, about 16:1, about 17:1, about 18:1, about 19:1, or about 20:1. In some embodiments, the composition further comprises an emulsifier, a non-ionic surfactant, or both that can allow for a greater variance in the ratio of poly(ethylene glycol) to viscoelastic polymer included in an exemplary polymeric composition.

Turning now to the antioxidants included in the compositions of the presently-disclosed subject matter, in some embodiments, the antioxidant included in an exemplary polymeric composition is selected from the group consisting of trehalose, nicotinamide, ascorbic acid, N-acetylcysteine, sodium azide, pyridoxine, alpha tocopherol, tocopherol, hydrazine, glutathione, thiol, beta-carotene, lycopene, astaxanthin, thioredoxin, tocochromanol, plastoquinol, cyanine, dismutase, enzymes, catalase, divalent cations, zinc, magnesium, or combinations thereof. In some embodiments, the antioxidant is trehalose. In some embodiments, the antioxidant is included in the composition at a concentration of about 0.001 wt % to about 10 wt %. Further, in some embodiments, the antioxidant is included in the composition as a plurality of antioxidant particles such as, in some embodiments, antioxidant particles having a diameter of about 50 nm to about 1000 nm.

To assist in the polymerization of the components of the compositions, once combined, in some embodiments, an initiator is further included in the compositions to initiate and/or promote polymerization of the poly(ethylene glycol) and the viscoelastic polymer. The initiator can be a photoinitiator or an enzyme. In some embodiments, the initiator is a photoinitiator and is selected from the group consisting of 2-hydroxy-4'-(2-hydroxyethoxy)-2-methylpropiophenone, eosin Y, triethanolamine, 1-vinyl-2-pyrrolidinone, and combinations thereof. In some embodiments of the compositions that make use of a photoinitiator, the viscoelastic polymers include a photo-crosslinking moiety that is capable of interacting with other components of the compositions (e.g., the poly(ethylene glycol) and assisting in the polymerization of the compositions.

To allow the compositions of the presently-disclosed subject matter to be effectively utilized with the eye lens of a subject, in some embodiments, the components of the compositions are configured (e.g., tuned) to impart certain characteristics or properties on the polymeric compositions. For instance, in some embodiments, the compositions are configured such that the composition comprises a surface energy or tension of less than about 4 dyne/cm or greater than about 40 dyne/cm, such that the adherence of proteins and cells to the compositions is mitigated. As another example, in some embodiments, the compositions are configured to have an elasticity of about 50 N/m to about 1000 N/m so as to reduce any potential interference with the shape of the natural eye lens of a subject. Further, in some embodiments, the composition has an osmolarity of about 281 mOsm to about 350 mOsm that allows the composition to be substantially isosmotic with the vitreous gel of an eye. Moreover, oxygen permeability is another property that can be adjusted in the compositions described herein and, in some embodiments, is from about 1% to about 80% in order to provide a composition that sufficiently reduces oxidative damage to the lens, and prevents the establishment of a perilenticular oxygen gradient. As yet another example of a tunable property, in some embodiments, the composition is thermally stable between a temperature of about 33° C. to about 37° C., such that the compositions are biocompatible and stable in the eye of a subject.

Further provided, in some embodiments of the presently-disclosed subject matter, are methods of synthesizing a composition such as those described herein. In some embodiments, a synthesis method is provided that includes the steps of heating an amount of water, adding a buffering agent to the water to thereby form a buffer solution (e.g., phosphate-buffered saline or a 2-[4-(2-hydroxyethyl)piperazin-1-yl]ethanesulfonic acid (HEPES) buffering solution); mixing a poly(ethylene glycol) and a viscoelastic polymer into the buffer solution to thereby form a reactive mixture; adding an antioxidant to the reactive mixture; and then removing suspended gas bubbles from the reactive mixture before allowing the reaction mixture to polymerize. In some embodiments, an emulsifier, a non-ionic surfactant, or both are also added to the reactive mixture. Additionally, in certain embodiments, an initiator, such a photoinitiator, an enzyme, or a combination thereof, is further added to the reaction mixture to assist in and provide control over the polymerization of the reaction mixture. For example, in some embodiments, the initiator included in the reactive mixture is a photoinitiator, such that, after the step of removing the suspended gas bubbles, the reactive mixture is exposed to electromagnetic radiation (e.g., visible light, ultraviolet light, or combinations thereof) to polymerize the compositions.

Still further provided, in some embodiments of the presently-disclosed subject matter, are methods of reducing oxidative damage to an eye lens of a subject. In some embodiments, a method of reducing oxidative damage to an eye lens of a subject is provided that includes first providing a composition including a poly(ethylene glycol), a viscoelastic polymer, and an antioxidant, where the composition has a refractive index of about 1.30 to about 1.40 in polymerized form. Then, the composition is administered to the eye lens of the subject. In some embodiments, the therapeutic methods can further include the step of polymerizing the composition subsequent to administering the composition to the eye lens of the subject. For example, in some embodiments, the composition further includes a photoinitiator, such that, once the composition is administered to a subject, the composition and the eye of a subject can be exposed to an amount of electromagnetic radiation and the composition can be polymerized within the eye of a subject. In some embodiments, the step of administering the composition comprises injecting the composition through a needle (e.g., a 25 gauge to 27 gauge needle) or other applicator into the eye of a subject.

Further features and advantages of the presently-disclosed subject matter will become evident to those of ordinary skill in the art after a study of the description, figures, and non-limiting examples in this document.

DESCRIPTION OF EXEMPLARY EMBODIMENTS

Figure 1:
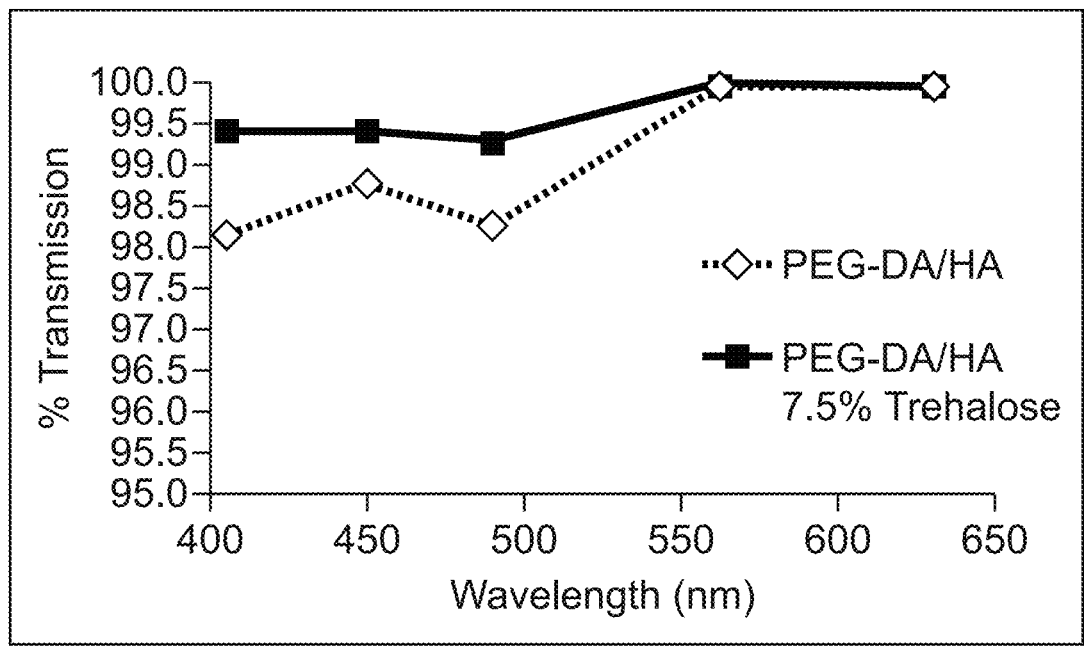
FIG. 1 is a graph showing the percent transmission of light as a function of the wavelength of light through a polymeric composition comprised of a mixture of poly (ethylene glycol)-diacrylate and hyaluronic acid (PEG-DA/HA) and a polymeric composition comprised of PEG-DA/HA including 7.5 wt % trehalose.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, the definitions set forth herein are provided to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a protein" includes a plurality of such proteins, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±50%, in some embodiments±40%, in some embodiments±30%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10"

is also disclosed. It is also understood that each unit between two particular units are also disclosed. For example, if 10 and 15 are disclosed, then 11, 12, 13, and 14 are also disclosed.

Vitrectomies, or the surgical removal of some or all of the vitreous gel from the eye, are routinely performed to treat a number of eye disorders, including diabetic eye disease. Despite the usefulness of vitrectomies in treating those disorders, however, the removal of the vitreous gel also routinely results in the formation of cataracts, either during the early post-operative period or during the late post-operative period. In particular, during the early post-operative period, prolonged contact of gas bubbles with the posterior lens surface results in the lens surface being exposed to an increased amount of oxygen that, in turn, causes in damage to the lens. During the late post-operative period, that exposure to oxygen then further takes the form of oxidative stress, which only serves to further damage the lens of the eye. In this regard, the attenuation of oxidative stress is thought to potentially provide a means to reduce cataract formation and lens opacity following a vitrectomy, and many antioxidant-containing compositions such as intraoperative irrigation solution, topical drops, and oral antioxidants have been developed to attempt to combat the oxidative stress that follows a vitrectomy. Nevertheless, the functionality of those prior compositions has been limited by the fact that the prior compositions had an effectiveness that was short in duration (e.g., minutes) or were entirely ineffective in preventing cataracts and lens opacities.

To that end, the presently-disclosed subject matter is based, at least in part, on the discovery that a polymeric composition can be produced that has controlled oxygen permeability and can function as an oxygen barrier, but that is also biocompatible, such that it can be inserted into the eye of a subject and can offer a noninvasive option for reducing oxidative damage to the eye lens after a vitrectomy. In some embodiments, the presently-disclosed subject matter thus includes compositions and methods for reducing oxidative damage. In particular, the presently-disclosed subject matter includes compositions and methods for reducing oxidative damage that make use of a combination of polymeric materials and an antioxidant for protecting an eye lens from oxidative damage. In some embodiments, a polymeric composition is provided that comprises a poly(ethylene glycol), a viscoelastic polymer, and an antioxidant. In this regard and as described further below, in some embodiments, the composition is a gel or, in other words, a semi-solid substance that exhibits viscous and/or elastic properties, and that is configured to cover an eye lens and reduce oxidative damage to the eye lens.

The type and amounts of poly(ethylene glycol) selected for use in the compositions of the presently-disclosed subject matter can, in some embodiments, vary depending on the intended use of the composition and can be tuned to impart desired properties on the composition. In some embodiments, the poly(ethylene glycol) has a molecular weight of about 2000 Da, about 3000 Da, about 4000 Da, about 5000 Da, about 6000 Da, about 7000 Da, about 8000 Da, about 9000 Da, about 10000 Da, about 11000 Da, about 12000 Da, about 13000 Da, about 14000 Da, about 15000 Da, about 16000 Da, about 17000 Da, about 18000 Da, about 19000 Da, or about 20000 Da, such that a poly(ethylene glycol) having a particular molecular weight can be selected so as to ensure sufficient accumulation of the viscoelastic polymer (e.g., polysaccharide) in the polymeric composition, to ensure that the composition has low protein adhesion, and/or to ensure that the composition is sufficiently water-soluble and biocompatible, as described in further detail below. In some embodiments, the poly(ethylene glycol) concentrations included in the compositions are kept low so that poly(ethylene glycol) is used efficiently in the synthesis of the polymeric composition. In some embodiments, the poly(ethylene glycol) is included in an exemplary polymeric composition at a concentration of about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, or about 150 mg/mL.

Furthermore, in some embodiments of the polymeric compositions, the poly(ethylene glycol) further comprises acrylate moieties, such as, for example, the acrylate moiety that is included in poly(ethylene glycol)-diacrylate (PEG-DA), and which assists in the assembly of the complete polymeric composition. In this regard, the term "poly(ethylene glycol)" is thus used to refer to poly(ethylene glycol) molecules alone, but is further inclusive of poly(ethylene glycol) materials having additional functional groups, such as PEG-DA and the like.

With respect to the viscoelastic polymers included in the compositions of the presently-disclosed subject matter, the term "viscoelastic polymer" is used herein refer to a polymer that is capable of imparting viscoelastic properties on the composition, where the term "viscoelastic" generally refers to a substance that exhibits both viscous and elastic properties. In some embodiments, the term "viscoelastic polymer" thus refers to a substance (e.g., a polysaccharide) that forms a viscoelastic composition when it reacts with poly(ethylene glycol).

Similar to the poly(ethylene glycol) portion of the polymeric compositions, in some embodiments, the types of viscoelastic polymers included in the compositions can also vary depending on the types and amount poly(ethylene glycol) that are used in a particular composition and/or the intended use of a particular polymeric composition. In some embodiments, the viscoelastic polymer is a polysaccharide. In some specific embodiments, the viscoelastic polymer is selected from hyaluronic acid or a salt thereof, hydroxymethylpropyl cellulose, chondroitin sulfate, polyacrylamide, collagen, dextran, heparin, agarose, chitosan, or combinations thereof, as such viscoelastic polymers have been found to impart sufficient viscoelasticity on a composition of the presently-disclosed subject matter. Typically, however, the viscoelastic polymer is selected so that when it is mixed with other components, such as the poly(ethylene glycol), it creates a composition having one phase and is optically pure.

In addition to selecting a particular type of visco-elastic polymer for a particular application, in some embodiments, the concentration or amounts of viscoelastic polymer included in an exemplary composition can also be varied to impart desired properties on an exemplary polymeric composition. For instance, in some embodiments, hyaluronic acid is included in an exemplary polymeric composition as the viscoelastic polymer at a concentration of about 5 mg/mL, about 6 mg/mL, about 7 mg/mL, about 8 mg/mL, about 9 mg/mL, about 10 mg/mL, about 11 mg/mL, or about 12 mg/mL, about 13 mg/mL, about 14 mg/mL, or about 15 mg/mL In some embodiments, the viscoelastic polymer is hydroxymethylpropyl cellulose, which, in some embodiments, is included in an exemplary polymeric composition at a concentration of about 1 mg/mL, about 5 mg/mL, about 10 mg/mL, about 15 mg/mL, about 20 mg/mL, about 25 mg/mL, about 30 mg/mL, about 35 mg/mL, or about 40 mg/mL. In other embodiments, the viscoelastic polymer includes hydroxymethylpropyl cellulose having a viscosity of about 200 cP to 5600 cP, when measured at a 2% concentration in water at room temperature (i.e., 20° C.), and, in some embodiments, the hydroxymethylpropyl cellulose has a molecular weight of about 200,000 Da. In further embodiments, exemplary polymeric compositions can include other viscoelastic polymers including, but not limited to, chondroitin sulfate at a concentration of about 25 to about 40%, polyacrylamine at a concentration of about 0.5% to about 25%, collagen at a concentration of about 1% to about 3%, agarose at a concentration of about 0.5% to about 5%, or chitosan at a concentration of about 0.5% to about 10%.

In some embodiments of the polymeric compositions, to further enhance the ability of the viscoelastic polymer described herein to be incorporated into and effectively used in a polymeric composition of the presently-disclosed subject matter, the viscoelastic polymers can be combined with and/or included with certain functional moieties (e.g., a photo-crosslinking moiety) that are capable of interacting with the other components of the composition. For example, in some embodiments, the hydroxymethylpropyl cellulose included in an exemplary composition can vary depending on the intended use of the composition and can include hydroxymethylpropyl cellulose linked to other functional moieties that assist in the assembly of the polymeric compositions. For instance, in some embodiments, the hydroxymethylpropyl cellulose included in the compositions is hydroxymethylpropyl cellulose acrylate. In this regard, in some embodiments, the viscoelastic polymers are provided with moieties that are configured to interact with the poly(ethylene glycol) portions of the compositions and allow the viscoelastic polymers to bond and polymerize with the poly(ethylene glycol) component so as to form a gel having poly(ethylene glycol) and a viscoelastic polymer that are covalently cross-linked. In other embodiments, the viscoelastic polymer and/or poly(ethylene glycol) do not include such functional moieties, and the resulting gel is an interpenetrating network of the respective components, rather than a cross-linked gel. In some embodiments, depending on the amount and types of cross-linking moieties including in a composition, the resulting gel can include both cross-linked portions and interpenetrating polymer portions.

Regardless of the types and amounts of the poly(ethylene glycol) and visco-elastic polymer included in a polymeric composition of the presently-disclosed subject matter, in some embodiments, to further tune the properties of the compositions and provide a composition that can effectively be utilized in the eye and, more specifically, with the eye lens of a subject, the poly(ethylene glycol) and the viscoelastic polymer are included in the composition at a ratio of poly(ethylene glycol) to viscoelastic polymer is about 5:3, about 5:2, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1. For instance, in certain embodiments that make use of hyaluronic acid as a viscoelastic polymer, the ratio of poly(ethylene glycol) to hyaluronic acid is preferably between about 5:1 to about 15:1, and is more preferably about 10:1. In some embodiments that make use of hydroxymethylpropyl cellulose as a viscoelastic polymer, the ratio of poly(ethylene glycol) to hydroxymethylpropyl cellulose is about 5:3 to about 15:3, and is more preferably about 10:3. Furthermore, in some embodiments comprising agarose, chitosan, and/or collagen as a viscoelastic polymer, the ratio of poly(ethylene glycol) to viscoelastic polymer is preferably about 5:1 to about 15:1. Additionally, in some embodiments comprising chondroitin sulfate and/or polyacrylamide as a viscoelastic polymer, the compositions comprise a ratio of poly(ethylene glycol) to viscoelastic polymer of preferably about 5:3 to about 15:3. In some embodiments, to allow for a greater variance in the ratio of poly(ethylene glycol) to viscoelastic polymer, while still allowing the compositions of the presently-disclosed subject matter to exhibit certain desired properties in their final polymerized form, the compositions further include an emulsifier or non-ionic surfactant. In some embodiments, the emulsifier or non-ionic surfactant is selected from the polysorbate family, including polysorbate 20, polysorbate 40, or polysorbate 80.

Turning now to the antioxidants included in the compositions of the presently disclosed subject matter, the term "antioxidant" is used herein to refer to substances capable of inhibiting oxidation of molecules or, in other words, substances capable of inhibiting the transfer of electrons or hydrogen from a particular substance to an oxidizing agent. In some embodiments, the term "antioxidant" can thus be used interchangeably with the term "oxygen quenching substance." A non-limiting list of potential antioxidants that may be used in the compositions of the presently-disclosed subject matter include sodium azide, pyridoxine, tocopherols, hydrazines, glutathione, thiols, beta-carotene, lycopene and astaxanthin, thioredoxin, tocochromanols, plastoquinol, cyanine dyes, enzymes such as superoxide dismutase or catalase, or the divalent cations of zinc or magnesium. In some embodiments, the polymeric compositions described herein can comprise more traditional antioxidants such as, in some embodiments, trehalose, nicotinamide, ascorbic acid, N-acetylcysteine, sodium azide, pyridoxine, alpha tocopherol, tocopherol, hydrazine, glutathione, thiol, beta-carotene, lycopene, astaxanthin, thioredoxin, tocochromanol, plastoquinol, cyanine, dismutase, enzymes, catalase, divalent cations, zinc, magnesium, and the like. In some embodiments, the antioxidant included in the polymeric compositions is trehalose.

As will be appreciated by those of skill in the art, incorporating an antioxidant into a polymeric composition of the presently-disclosed subject matter functions to enhance the composition's ability to act as a barrier for oxygen and to neutralize reactive oxygen species. It has been determined, however, that including excessive amount of an antioxidant in an exemplary composition interferes with the polymerization of the compositions by quenching free radical polymerization processes. As such, in some embodiments, the compositions of the presently-disclosed subject matter comprise about 0.001 wt %, about 0.5, wt %, about 1.0 wt %, about 1.5 wt %, about 2.0 wt %, about 2.5 wt %, about 3.0 wt %, about 3.5 wt %, about 4.0 wt %, about 4.5 wt %, about 5.0 wt %, about 5.5 wt %, about 6.0 wt %, about 7.0 wt %, about 7.5 wt %, about 8.0 wt %, about 8.5 wt %, about 9.0 wt %, about 9.5 wt %, or about 10.0 wt % of an antioxidant.

In some embodiments of the presently-disclosed subject matter, the antioxidants are included in the compositions in powder form, particulate form, or combinations thereof. In some embodiments, the antioxidant can thus be homogeneously mixed throughout the polymeric composition so as to maximize the antioxidant or oxygen quenching effect of the composition without unduly affecting light transmission and liquid diffusion though the composition. For instance, in certain embodiments, the compositions can comprise antioxidant (e.g., trehalose) particles having a diameter of about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, or about 1000 nm, such that the particles can fill pores in the composition, and can therefore provide an additional benefit of further reducing oxygen and other gas diffusion through the composition. In this regard, in some embodiments, the antioxidants are selected such that the substances do not compromise the physical and optical attributes of the compositions.

To assist in the polymerization of the components of the compositions, once combined, in some embodiments, an initiator is further included in the composition to initiate and promote the polymerization of the poly(ethylene glycol) and the viscoelastic polymer. In some embodiments, the initiator is a photoinitiator, wherein the photoinitiator can initiate the polymerization of the composition upon exposure to electromagnetic radiation having a certain wavelength, such visible light, ultraviolet light, or a combination thereof. In other embodiments, the initiator is an enzyme that can initiate polymerization. For example, in some embodiments, the initiator is glucose oxidase that mediates a redox chain initiation of polymerization. In some embodiments, a minimum amount of initiator is added to polymerize the composition so as not to unduly interfere with the physical properties of the compositions described in more detail below.

In some embodiments that make use of a photoinitiator for promoting polymerization of the polymeric compositions, the photoinitiator is selected from the group consisting of 2-hydroxy-4'-(2-hydroxyethoxy)-2-methylpropiophenone (Irgacure® 2959, CIBA-GEIGY Corporation, Tarrytown, New York), eosin Y, triethanolamine (TEA), 1-vinyl-2-pyrrolidinone (NVP), or a combination thereof. In certain embodiments, the composition comprises only 2-hydroxy-4'-(2-hydroxyethoxy)-2-methylpropiophenone at a concentration of about 0.05 to about 0.1 w/v %. In other embodiments, the composition makes use of a solution of about 100 mg/mL of 2-hydroxy-4'-(2-hydroxyethoxy)-2-methylpropiophenone and 70% ethanol in water and, in some embodiments, about 7 µL to about 14 µL of the 2-hydroxy-4'-(2-hydroxyethoxy)-2-methylpropiophenone and 70% ethanol solution is then added per milliliter of composition. In further embodiments, the initiator comprises a mixture of eosin Y, triethanolamine (TEA), and N-vinyl pyrrolidinone (NVP), and in specific embodiments, may comprise 0.01 mM eosin Y, 0.1% to 1.5% TEA, and 37 nM NVP.

As described above, to allow the polymeric compositions of the presently-disclosed subject matter to be effectively utilized with the eye lens of a subject, in some embodiments, the respective components are selected and proportioned to achieve certain characteristics in the resulting composition. More specifically, in certain embodiments, the concentration and type of poly (ethylene glycol) as well as the concentration and type of viscoelastic polymer are adjusted to achieve certain characteristics in the resulting composition. For instance, in some embodiments, the amount and type of the components included in an exemplary composition are selected so that the resulting composition is biocompatible and stable in the eye, particularly, in some embodiments, at temperatures between about 33° C. to about 37° C. In some embodiments, the compositions are configured such that, when placed on the eye lens, the compositions remain stable for a time period of about 6 months or longer.

Further, in some embodiments, the compositions are also configured to have a particular viscosity, elasticity, oxygen permeability, osmolarity, and resistance to protein and cell adhesion. In some embodiments, an exemplary composition has a viscosity within a range that permits the composition to be injected through a needle, including, in some embodiments, 25 or 27 gauge needles. In this regard, in some embodiments, the compositions are also configured to be sufficiently elastic so as to not interfere with the accommodative ability of the eye lens. In some embodiments, for example, the polymeric compositions described herein have an elasticity of about 50 N/m to about 1000 N/m.

Oxygen permeability is another characteristic that can be adjusted in the compositions described herein. The oxygen permeability of some embodiments can be about 1%, 2%, 3%, 4%, or 5%, about 10%, about 20%, about 30%, about 40%, about 50%, about 60%, about 70%, or about 80%. In some embodiments, the oxygen permeability is from about 0.1% to about 10%, such that a composition is provided having a low oxygen permeability that, in turn, increases the composition's ability to prevent oxidative damage to the eye lens. In some embodiments, by providing such a composition, a barrier can thus be provided that is relatively oxygen impermeable, such that the composition can be used to reduce the formation of a perilenticular oxygen gradient from building up and potentially causing oxidative damage that can lead to or accelerate the formation of cataracts. Of course, in some embodiments, the permeability of the membrane, including the oxygen permeability, can be readily adjusted such that the compositions are permeable to certain fluids and ions, and do not block necessary substances from reaching the eye lens. In this regard, in some embodiments, the compositions are further configured to have an osmolarity of about 281 mOsm to about 350 mOsm to allow the compositions to be substantially isosmotic to vitreous humor of an eye.

In addition to the configurations described above, in some embodiments, the polymeric compositions are also configured to have surface tensions that prevent or mitigate proteins and cells from adhering to the composition. This characteristic, among other things, helps to ensure that the composition remains optically clear and does not pose long-term side effects when implanted on or applied to an eye lens of a subject. In some embodiments, the surface tension of the composition is less than about 4 dyne/cm. In some embodiments, the surface tension of the composition is greater than about 40 dyne/cm. In some embodiments, removal or decreasing the amount of poly(ethylene glycol) present in a particular composition leads to decreased biocompatibility due to increased protein adsorption and surface tension in the compositions.

The properties of each of the compositions of the presently-disclosed subject matter can readily be selected for a particular application and fine-tuned by varying the types and amounts of the components of the compositions and then testing for the desired properties using methods known to those skilled in the art. Typically, however, in each embodiment of the compositions, the components are selected so that the resulting composition is optically clear, does not interrupt light transmission, and does not cause glare or cause a loss of contrast. In this regard, in each embodiment, the compositions will generally exhibit greater than 95% transmission of light in the visible region (400-700 nm) upon polymerization. Additionally, in each embodiment, the compositions are configured such that, in polymerized form, the compositions have a refractive index that is similar to or the same that found in the eye lens of a subject, and thus, does not cause excessive, if any, refractive errors when it is applied to the eye lens. In this regard, in some embodiments, the compositions have a refractive index of about 1.30 to about 1.40, and preferably between about 1.30 and 1.60, and more preferably between about 1.33 and 1.36.

Of course, the various properties of the presently-described compositions can also be adjusted to best match the particular characteristics of an eye lens found in a particular subject. For instance, the elasticity and refractive index can be selected to correspond to those of the eye lens of a particular so that the eye lens' function is not unduly compromised when the present composition is applied thereto. The components can also be selected to adjust the non-quantitative characteristics of the composition. For instance, in some embodiments, the components are selected and combined such that the resulting composition can be spread smoothly, is cohesive and does not detach from the eye lens, and can be leveled into a desired shape. In this regard, by tuning the characteristics of the present composition to meet certain parameters, the composition can be placed on an eye lens in a minimally invasive manner, such as by injection, yet still provide a stable, biocompatible composition that is then able to prevent or reduce oxidative damage to an eye lens.

Further provided by the presently-disclosed subject matter are methods for synthesizing the compositions described herein. In some embodiments, a method is provided where an amount of water (e.g., ultra-pure de-ionized water) is first provided and heated to a boil so to remove any carbon dioxide that may be present in the water and act as a buffering system that may interfere with the final transparency of the compositions. After boiling, a buffering agent is then added to the water to thereby form a buffer solution (e.g., phosphate-buffered saline or a 2-[4-(2-hydroxyethyl)piperazin-1-yl]ethanesulfonic acid (HEPES). The poly(ethylene glycol) and the viscoelastic polymer are then mixed into the buffer solution to form a reactive mixture. An initiator, if necessary or desired, and the desired type and amount of antioxidant is then subsequently added to the reactive mixture. In some embodiments, the antioxidant can be provided in the form of particles by first spray drying a solution of the antioxidant particles (e.g., by using a Buchi B-90 nano spray dryer, Buchi Corporation, New Castle, DE) to produce sub-micron diameter (e.g., 100-200 nm) particles prior to introducing them into the reaction mixture. After inserting the various components into the reaction mixture, the mixture is then mixed and, to remove suspended gas bubbles that may compromise the physical or optical characteristics of the composition and may potentially expose the eye lens to oxygen, centrifuged for a period of time sufficient to remove the gas bubbles from the composition.

In some embodiments of the synthesis methods described herein, the reactive mixture is then allowed to react to form the gel or, in other words, a polymeric composition of the presently-disclosed subject matter. As described above, however, in some embodiments that make use of an initiator that provides the reactive mixture with the ability to polymerize, the initiator is then activated so as to initiate and promote the polymerization of the compounds. For example, in some embodiments that make use of a photo-initiator, after removing the gas bubbles from the compositions, the reactive mixture can be exposed to electromagnetic radiation (e.g., visible light, ultraviolet light, and combinations thereof) to polymerize the compositions.

Still further provided by the presently-disclosed subject matter are methods for reducing oxidative damage to an eye lens of a subject. In some embodiments, a method of reducing oxidative damage is provided that comprises the steps of providing a composition of the presently-disclosed subject matter and then administering the composition to the eye lens of a subject. In some embodiments, the composition is administered to a subject post-vitrectomy to reduce the oxidative damage to the eye lens that may otherwise be experienced by the at subject and that may potentially lead to the development of cataracts. Of course, those of skill in the art will appreciate that the present composition can also be placed on any tissue or surface requiring an oxygen barrier and can be used to reduce an amount of oxidative damage on those tissues or surfaces.

The terms "reduce," "reducing," or "reduction" when used herein in reference to oxidative damage are used to refer to any decrease or suppression in the amount or rate of oxidative damage to the tissue of a subject, such as the eye lens. Of course, it is understood that the degree of reduction need not be absolute (i.e., the degree of inhibition need not be a complete prevention of oxidative damage) and that intermediate levels of a reduction in oxidative damage are contemplated by the presently-disclosed subject matter. As such, in some embodiments, the reduction in oxidative damage can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%.

For administration of a composition as disclosed herein, in some embodiments, the presently-described polymeric compositions can be administered to a subject using a variety of different applicators including needles, plastic, ceramic, or metal applicators, and the like, and can be administered in unpolymerized form (e.g., as a viscous liquid), in a partially-polymerized form, or in a fully polymerized form. For example, in some embodiments, an exemplary composition is administered to a subject by directly injecting the unpolymerized composition through a small bore needle, such as a 25 or 27 gauge needle, into the eye of a subject adjacent to or onto the posterior side of the eye lens. In some embodiments, the composition can then be manipulated by spreading or leveling the composition once it has been applied to a surface, and, if a photoinitiator was included, can then be polymerized by exposing the composition and the eye to electromagnetic radiation. As another example, in some embodiments, the composition can be administered by first molding and polymerizing the composition into a desired shape, and then surgically placing the molded composition directly on the eye lens. As yet another example, in some embodiments, an exemplary composition can also be administered to a subject by using a small amount unpolymerized gel to fuse or adhere to a pre-formed, polymerized or partially-polymerized gel to the eye lens of a subject.

Regardless of the particular mode of administration used in accordance with the methods of the presently-disclosed subject matter, the polymeric compositions described herein are typically administered in an amount effective to achieve the desired response (i.e., a reduction in oxidative damage). As such, the term "effective amount" is used herein to refer to an amount of the therapeutic composition (e.g., a polymeric composition) sufficient to produce a measurable biological response (e.g., a reduction in oxidative damage). Actual dosage levels of active ingredients in a therapeutic composition of the presently-disclosed subject matter (e.g., the antioxidants) can be varied so as to administer an amount of the polymeric composition that is effective to achieve the desired therapeutic response for a particular subject and/or application. The selected dosage level and amount of the antioxidant and the other components of the polymeric composition will depend upon a variety of factors including the activity of the antioxidant, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art of medicine.

In addition to being capable of use in a method of reducing oxidative damage in an eye of a subject, in some embodiments, the compositions described herein can further be used to provide other therapeutic benefits. For example, because the refractive index of the presently-described polymeric compositions are similar to the crystalline lens of a subject, in some embodiments, the posterior surface of the polymeric composition can be sculpted upon polymerization to change the refractive power of the existing lens of the subject. In this regard, and considering that 25% of the US population has myopia with 30% of that affected population having high (greater than −6D) myopia, the physicochemical properties of the gel can be used to provide enhanced refractive properties to that population. In this regard, and without wishing to be bound by any particular theory or mechanism, it is further believed that doing so is advantageous as the administration of the polymeric composition will place it closer to the optical nodal point, thus allowing for a better and more physiological correction of the myopia, for an improved maintenance of the accommodative property of the lens, and for the avoidance of ocular complications of piggyback intraocular lenses and the like.

As another example of the therapeutic use of the polymeric compositions described herein, in some embodiments, the polymeric composition can further be combined with one or more additional therapeutic agents such that the compositions can be used to deliver the therapeutic agents directly into the intraocular media in a slow release manner. In this regard, and considering that the compositions are typically configured to be administered intraoperatively during vitrectomy surgery, routine postoperative regimens of therapeutic agents (e.g., steroids, NSAIDS, cycloplegics, and antibiotics) can be incorporated into the compositions and delivered postoperatively along with the compositions. Of course, the therapeutic agents that can be incorporated into such a polymeric composition are not limited to such postoperative agents, but can also include therapeutic agents such as anti-VEGF drugs for retinal vascular diseases and/or anti-tumor, anti-fibrotic, anti-inflammatory agents, immunomodulators, encapsulated cells, and/or genetic materials that are useful in treating a number of diseases or disorders in a subject.

As used herein, the term "subject" is inclusive of both human and animal subjects. Thus, veterinary uses are provided in accordance with the presently disclosed subject matter and the presently-disclosed subject matter provides methods for preventing oxidative damage in mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The presently-disclosed subject matter is further illustrated by the following specific but non-limiting examples.

EXAMPLES

Example 1—Synthesis of Oxygen Barrier Composition

To synthesize an exemplary oxygen barrier composition, in some embodiments, 1 mL of the composition is prepared by initially preparing a buffer solution by boiling 100 mL of ultra-pure de-ionized water (18 MΩ resistance) for one-half hour and then adding 2-[4-(2-hydroxyethyl)piperazin-1-yl] ethanesulfonic acid (HEPES, free acid version) to the de-ionized water to a final concentration of 10 mM. The pH of that solution is then adjusted to 7.2 using a minimal amount of sodium hydroxide. A separate eosin Y solution is then prepared by dissolving 6.4 µL eosin Y in 10 mL of ultra-pure de-ionized water (18 MΩ resistance) by sonication in a bath sonicator for 30 minutes. At the same time, trehalose particles having a sub-micron size are prepared by mixing 1 g of trehalose and 0.025 w/v % Tween 20 in ultra-pure de-ionized water (18 MΩ resistance). That mixture was then spray dried using a Buchi B-90 nanospray dryer (BÜCHI Labortechnik, Flawil, Switzerland) with a 5.5 µm mesh at 80° C., 100 L/min airflow, a fast flow rate, and one-hundred percent spray capacity until all of the solution was sprayed. The resulting trehalose particles were then removed from the collection drum with a Teflon® (E. I. Du Pont De Nemours and Company, Wilmington, De) spatula, and were be stored at −20° C. until use.

Upon preparation of each of the foregoing solutions and particles, the oxygen barrier composition was then synthesized by adding 100 mg/mL of polyethylene glycol-diacrylate (PEG-DA) and 10 mg/mL of hyaluronic acid to 1 mL of the HEPES buffer and stirring for 1 hour using an overhead stirrer. N-vinyl pyrrolidinone (3.5 µl/ml), the eosin Y solution (10 µl/ml), and triethanolamine (8.9 µl/ml) were then added to the mixture of PEG-DA and the mixture was mixed with a spatula for 1 minute. 7.5 w/v % of the trehalose particles were then added and the mixture was again mixed with a spatula for 1 minute. Bubbles were then removed from the mixture by centrifuging the mixture for 1 to 2 min at 300 RPM. The mixture was then placed in an single well of a well plate, and was exposed to a LED light source emitting light having a wavelength of 520 nm and an energy of about 50 mW/cm$^2$ for 60 to 90 seconds. At that time, the polymerization was sufficiently complete and formed an oxygen barrier composition having the following formulation: 100 mg/mL poly(ethylene glycol)-diacrylate (PEG-DA); 10 mg/mL hyaluronic acid (HA); 7.5 w/v % trehalose sub-micron particles produced via spray-drying; and, for purposes of photo-initiation, N-vinyl pyrrolidinone (NVP, 3.5 µL/ml), triethanolamine (TEA, 8.9 µL/ml), and Eosin Y (10 µL/ml of Eosin Y stock solution).

Example 2—Characterization and Analysis of the Oxygen Barrier Composition

To characterize and analyze the synthesized oxygen barrier composition produced in Example 1, and to determine whether the synthesized oxygen barrier composition has desirable optical and physical characteristics that would allow it to be used to prevent oxidative damage to the lens of an eye, a number of measurements were taken. From those measurements, the components of the composition could then be varied and adjusted, if necessary, to produce an oxygen barrier composition having the desired properties (e.g., optical, biocompatibility, etc.).

In the characterization of the composition, osmolarity of the pre-gel composition was first assessed using 50 μL of sample in a 5004 MICRO-OSMETTE™ Automatic High Sensitivity 50 μL Osmometer (Precision Systems, Inc.) The osmolarity was calculated as an average of 5 readings (280 mOs, 289 mOs, 312 mOs, 296 mOs, 334 mOs) from the osmometer, and was measured to be 302.2±21.3 mOsm, which was close to or matched the osmolarity typically observed in the vitreous humor of a human eye.

The gels forming the oxygen barrier compositions absorb light due to the presence of hyaluronic acid and trehalose and, as such, the transmission of light through the compositions was assessed using gels formed in 48-well plates and a BioTek plate reader (Winooski, VT) operating in single wavelength mode. In those experiments, the transmission of light through the gel exceeded 95% in light wavelengths ranging from 400-700 nm (FIG. 1). The readings were further confirmed using a Cary 100 UV-visible spectrometer with a film holder attachment (Agilent Technologies, Santa Clara, CA), and it was observed that there was significant UV light absorption due to the HA and trehalose components of the compositions.

In addition to measuring the osmolarity and light transmission, the surface energy of the compositions was further measured using a sessile drop method, and was found to be approximately 1 dyne/cm as the contact angle was too low for measurement and was therefore assumed to be 0-1 dyne/cm. The elasticity of the pre-gel formulation of the composition was also measured using a Haake Caber extensional rheometer (Thermo Fisher Scientific, Inc., Waltham, MA) and was found to be 41.5 pa by fitting the raw data to a power model for best fit.

Figure 2:
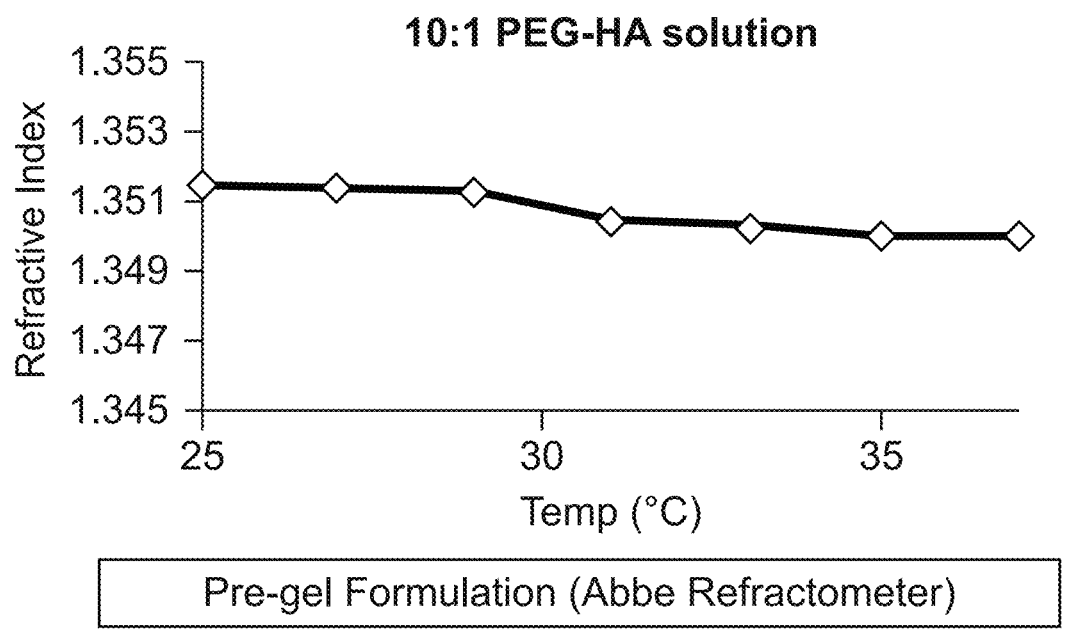
FIG. 2 is a graph showing the refractive index of a polymeric composition of the presently-disclosed subject matter comprised of 100 mg/mL poly(ethylene glycol)-diacrylate (PEG-DA), 10 mg/mL hyaluronic acid (HA), and 7.5 w % trehalose sub-micron particles.

Refractive Index measurements of the compositions were also performed using an Anton Paar (Ashland, VA) Abbemat refractometer. The refractive indexes of the photopolymerized gels were found to be in a preferred range of 1.33-1.36, which was equivalent to the refractive index of the natural crystalline lens (1.338-1.357) of an eye of a subject. The refractive indexes of the gels were also observed to remain stable within a wide range of temperature changes between 25-40° C. (FIG. 2).

To assess and fine tune the optical purity of the compositions, a number of experiments were further undertaken in which various buffering systems were assessed. Upon analysis of the results from those experiments, it was observed that a "low-sodium" HEPES buffer was preferable as buffered solutions containing increased sodium levels resulted in cloudiness in the gels. Additionally, it was found that it was preferable to use ultra-pure water (resistance of 18 mOhms) to generate the HEPES buffer solution. It was further found that it was preferable to boil the HEPES buffer for approximately 30 minutes as boiling for that amount of time allowed for the removal of gasses prior to adjusting the buffer to desired pH, a process that, in turn, minimized pH adjustments by removing dissolved carbon dioxide ($CO_2$) from the water.

Ascorbic acid is known to exist in high concentration in the aqueous humor of the eye and, as such, further experiments were undertaken to determine the resistance of the compositions to the high ascorbate levels that would be found within intraocular fluids. Briefly, the gelled compositions were stored in 1.4 mM ascorbate in 37° C. for two months with the ascorbate solution being changed for freshly made solution every day. During that time, the degree of yellowing was assessed visually by placing each gel over a white background and then comparing that gel to a control gel with no ascorbate exposure. Upon analysis of those results, it was observed that the compositions maintained their clarity and optical transmission characteristics within the solutions containing high ascorbate (1.4 mM) for more than two months, indicating the compositions would also be resistant to the ascorbate levels typically found in intraocular fluids.

To assess the amount of trehalose particles that could be incorporated into the compositions without interfering with the photo-polymerization capabilities of the compositions, escalating concentrations of Trehalose were incorporated into the pre-gel compositions using the synthesis procedures described above and photo-polymerization of each composition was then attempted. In these experiments, it was observed that about 6% to about 10% w/v of the antioxidant could be incorporated into the compositions without interfering with photo-polymerization, with 7.5 w/v % being found to be the preferred concentration of trehalose that could be incorporated into the gel formulation to act as an antioxidant without interfering with photo-polymerization.

Figure 3:
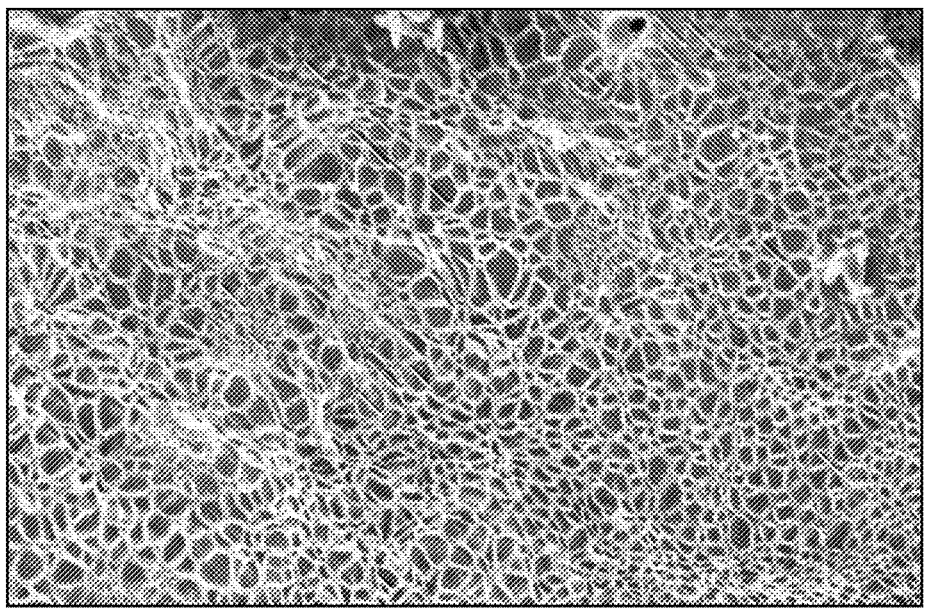
FIG. 3 is a scanning electron microscopy (SEM) image of a lyophilized poly(ethylene glycol)-diacrylate and hyaluronic acid hydrogel in accordance with the presently-disclosed subject matter comprised of 100 mg/mL poly (ethylene glycol)-diacrylate (PEG-DA), 10 mg/mL hyaluronic acid (HA), and 7.5 w % trehalose sub-micron particles.
Figure 4:
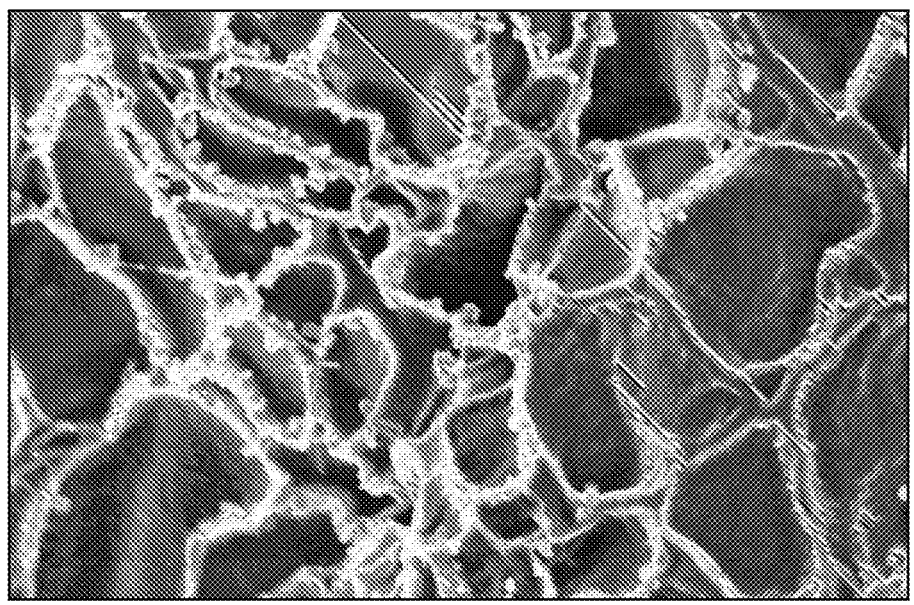
FIG. 4 is a SEM image of a polymeric composition of the presently-disclosed subject matter comprised of 100 mg/mL poly(ethylene glycol)-diacrylate (PEG-DA), 10 mg/mL hyaluronic acid (HA), and 5 w % trehalose sub-micron particles.
Figure 5:
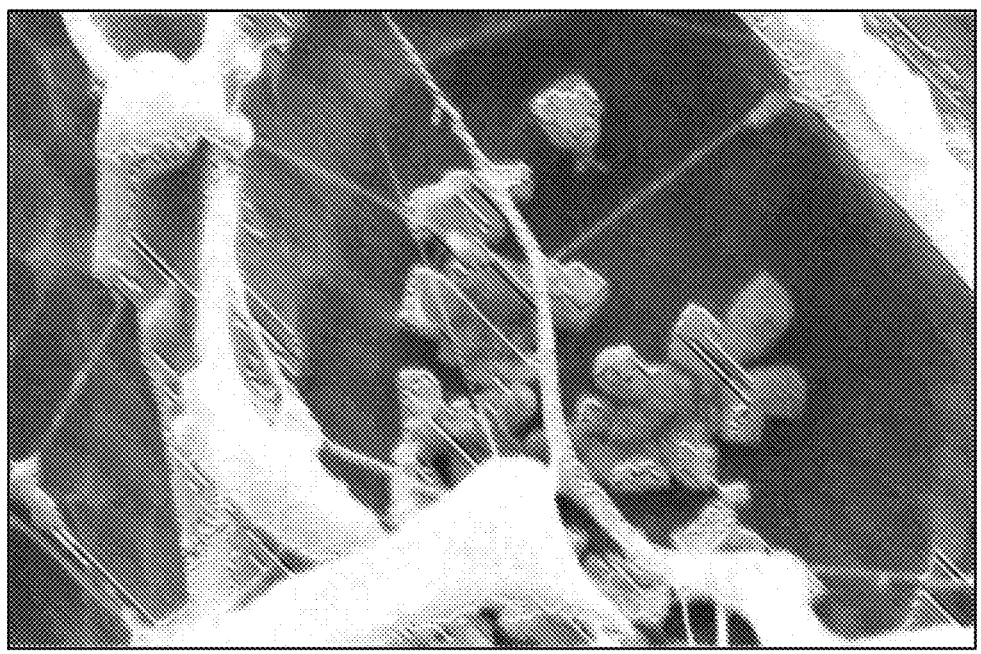
FIG. 5 is a higher magnification of the SEM image shown in FIG. 4, and further showing the trehalose particles positioned in the pores of the polymeric composition.

To further analyze the oxygen barrier compositions, scanning electron microscopy (SEM) was used. In those experiments, gels were initially formed as described herein above and were then lyophilized overnight to remove water. The dried gels were then affixed to a stainless steel sample pedestal using conductive carbon paint. Sample gels were then coated with a thin (approximately 0.2 nm) coating of gold/palladium alloy using a sputter coater, and the samples were subsequently imaged using a Zeiss Supra 35 Field emission scanning electron microscope operating at 2 kV beam voltage. The resulting gels appeared to be consistent with the structure and morphology of hydrogels with the trehalose particles positioned in the pores of the hydrogels (FIGS. 3-5).

Figure 6:
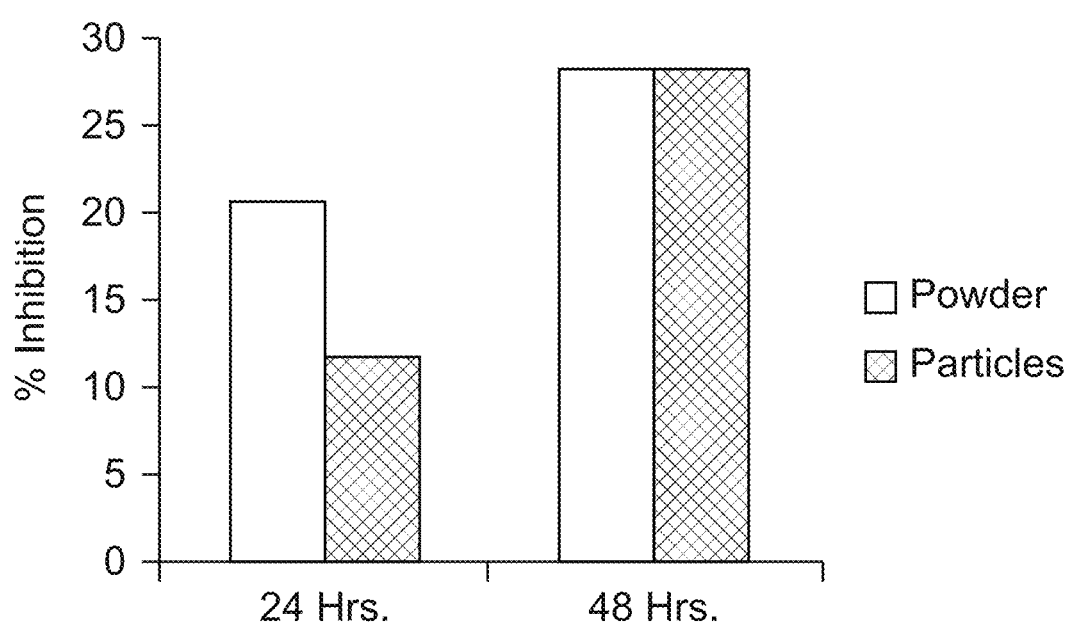
FIG. 6 is a graph showing the antioxidant capacity of trehalose particles versus the antioxidant capacity of trehalose powder, where the antioxidant capacity of the particles and powder was measured as the percent inhibition of oxygen radicals over two time periods.

With further respect to the trehalose particles, and without wishing to be bound by any particular theory, it was believed that trehalose particles may be more amendable to use as an antioxidant as compared to trehalose in powder form because the trehalose particles were thought to provide a slow release of the antioxidant. To further examine this belief, the antioxidant capacity of trehalose powder and trehalose particles was measured using a diphenylpicrylhydazil (DPPH) assay according to standard protocols. More specifically, in the assay, a sample of the compositions was assessed for its ability to quench the stable organic free radical in DPPH as measured by the decay of DPPH absorbance at 530 nm. Samples were measured after 24 hours and 48 hours in solution and, upon observing the results, it was found that trehalose particles had about the same antioxidant capacity as trehalose powder, but that trehalose particles allowed for an extended response (FIG. 6).

Figure 7:
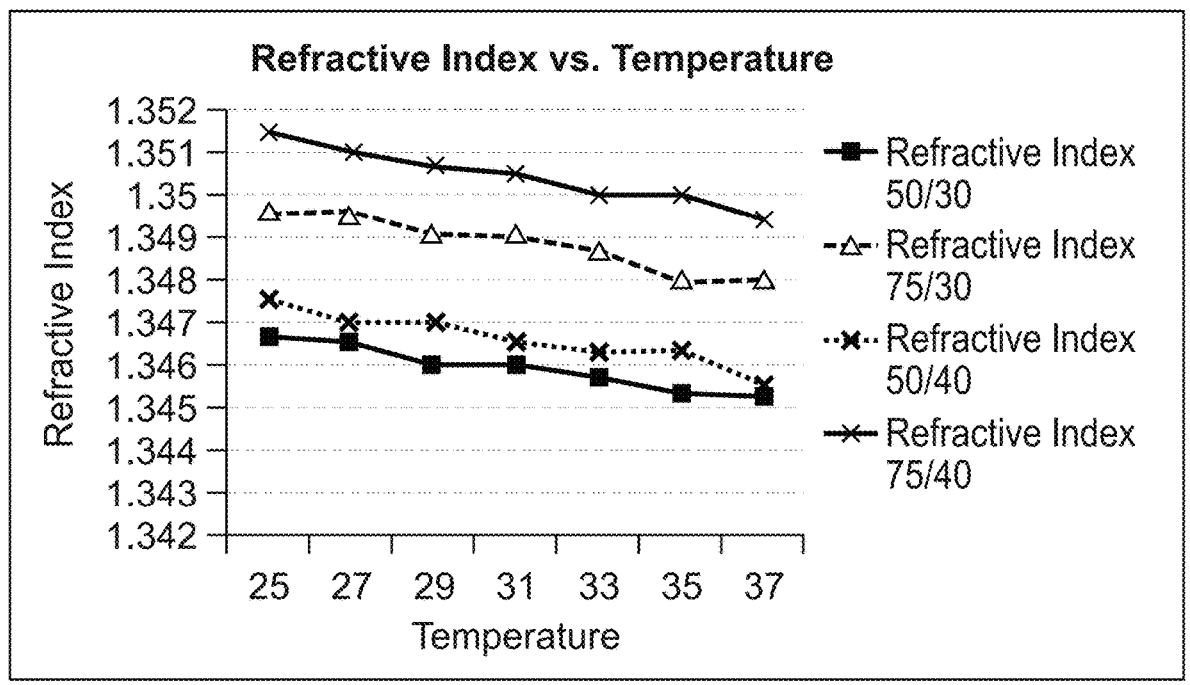
FIG. 7 is a graph showing the variation in the refractive indexes of polymeric compositions of the presently-disclosed subject matter as a function of temperature.

To then assess the extent to which the ratios of PEG-DA to HA in the compositions could be varied without affecting the compositions, ratios of PEG-DA to HA of 50/30, 75/30, 50/40, and 75/40 were used to synthesize oxygen barrier compositions according the above-described synthesis methods and the refractive indexes of each of the gels were measured on a Metricon 2010/M prism coupler (Metricon Corporation, Pennington, NJ). It was found that the refractive index of the gels did not vary greatly upon varying the ratios of PEG-DA to HA (FIG. 7). Using similar experiments in which the various concentrations of trehalose were tested along with various buffer solutions using a handheld refractometer, it was also observed that the addition of trehalose did not change the refractive index of the resulting gel compositions (Table 1).

TABLE 1

| 10:1 PEG-DA:HA Gel | Refractive Index (nD) |
|---|---|
| With 5% w/v trehalose (PBS) | 1.34695 |
| With 5% w/v trehalose (HEPES) | 1.34655 |
| No Trehalose (HEPES) | 1.34085 |

To further assess the gel compositions and, in particular, the ability of the gel compositions to be used to effectively act as an oxygen barrier, the gel composition was used to coat a dissolved oxygen probe attached to a Beckman 500 series dissolved oxygen meter (Beckman Coulter, Inc., Brea, CA). Upon coating the probe and placing it into deionized water, it was observed that the gel coating was able to reduce the dissolved oxygen being measured from 10% to 0.2% in 9 minutes time (Table 2), thus indicating that the gel compositions can effectively be used as an oxygen barrier.

TABLE 2

| % $O_2$ | Time |
|---|---|
| 10.9 | 1323 (0 Min) |
| 15.04 | 1324 (+1 Min) |
| 2.92 | 1325 (+2 Min) |
| 0.104 | 1326 (+3 Min) |
| 0.000 | 1327 (+4 Min) |
| 0.067 | 1328 (+5 Min) |
| 0.209 | 1329 (+6 Min) |
| 0.0565 | 1330 (+7 Min) |
| 0.07 | 1331 (+8 Min) |
| 0.214 | 1332 (+9 Min) |

To assess whether the compositions would be capable of administration to an eye of a subject through a needle (e.g., a 25-gauge needle typically used to inject solutions into an eye), the viscosity of the formulation was measured by placing 1 mL of the gelled composition in a Brookfield DV-II Rotational viscometer (Middleboro, Ma). The formulation viscosity was found to be in the range from 8000-12000 cP, which would allow the composition to be applied through a 25 G cannula and would also allow the composition to be used with conventional vitrectomy instrumentation.

Figure 8:
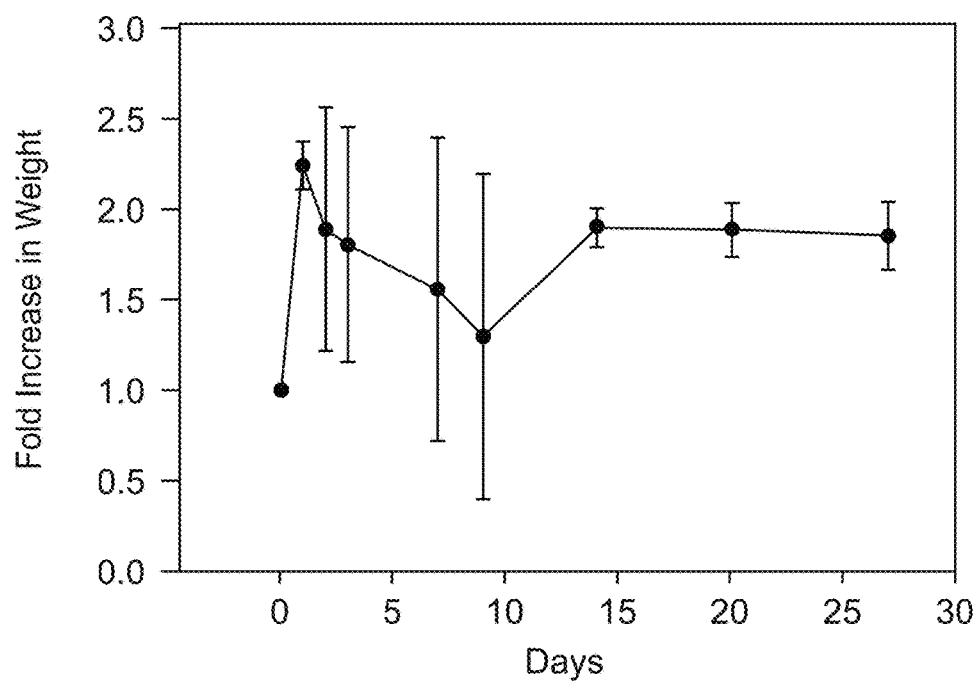
FIG. 8 is a graph showing changes in weight of a polymeric composition of the presently-disclosed subject matter after soaking the polymeric composition in water for a period of 30 days.
Figure 9:
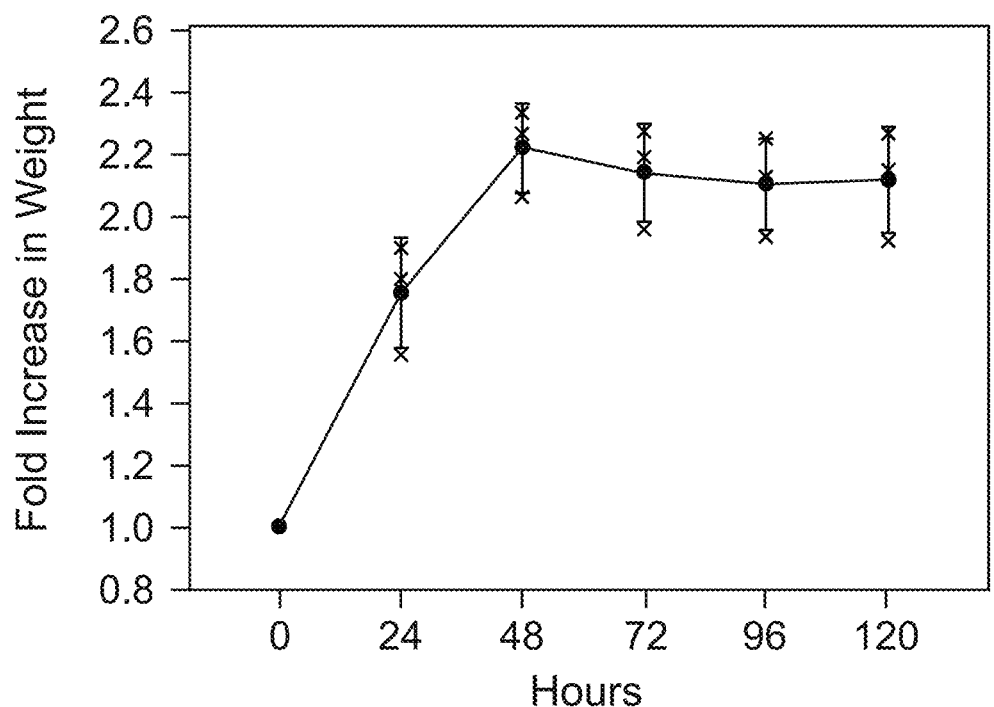
FIG. 9 is a graph showing the changes in weight of a polymeric composition of the presently-disclosed subject matter over an initial 120-hour period after soaking the polymeric composition in water.

During the course of the foregoing experiments, it was observed that the compositions generally maintained their integrity and physicochemical properties and were able to do so for greater than 1 year as measured by manipulating the gel with a spatula after storing for 1 year at 4° C. After being polymerized, however, it was observed that the compositions swell due to the absorption of the water. These observations were subsequent to soaking the gelled compositions in water and then measuring the weight of the gel at various time points. That soaking resulted in a 2.2±0.13 fold increase in gel weight (FIG. 8), with the majority of the swelling occurring within the first 24 to 48 hours (FIG. 9).

As the gels were to be placed in the eyes of subjects, experiments were also undertaken to assess the proper method for sterilization and the extent of protein adsorption of the gelled compositions. To determine the proper method for sterilization, gamma irradiation of hyaluronic acid before reconstituting the gel was initially employed; however, such gamma irradiation altered the physic-chemical properties of the gel and was therefore abandoned. Gas sterilization of the HA using ethylene oxide (EtO) gas was then assessed, with the remainder of the components used to make the gel being filter-sterilized using filters having a 0.2 micrometer pore size. It was observed that the compositions polymerized with the gas-sterilized hyaluronic acid and the filter-sterilized components and that the gelled compositions generally maintained their physicochemical properties. A slight increase in viscosity of the HA after EtO sterilization was measured using a viscometer, which correlated to a slight reduction in polymer molecular weight via gel permeation chromatography. However, no residual compounds or chemical modifications to the HA were detected from the sterilization, and the compositions gelled readily and maintained clarity.

To assess the extent of protein adsorption on the gels, studies were conducted by soaking the hydrogels in a 10 to 100 μg/μl BSA solution for 24 to 72 hours and then checking the adsorbed BSA on the gels with BCA protein assays. Those studies revealed that, during the swelling of the gels, proteins soaked into the gel along with water, but did not integrate into the gels themselves, and thus, were not retained within the structure of the gel and did not affect the optical clarity of the gels. It was further observed that the adsorbed proteins could be soaked out of the gels over time.

Finally, cell attachment studies were further conducted with the gels to analyze whether various cells would attach to the gels once implanted into the eyes of a subject. In this regard, 10,000 ARPE-19 cells (i.e., a retinal pigment epithelial cell line) and fibroblasts were seeded on gels maintained in serum containing standard culture media for those cells for 24 hours. Cell attachment was then determined using phase contrast microscopy and MTS assays. No cell attachment was noted at 24 hours for both cell types.

Example 3—Ex Vivo Analysis

Figure 10:
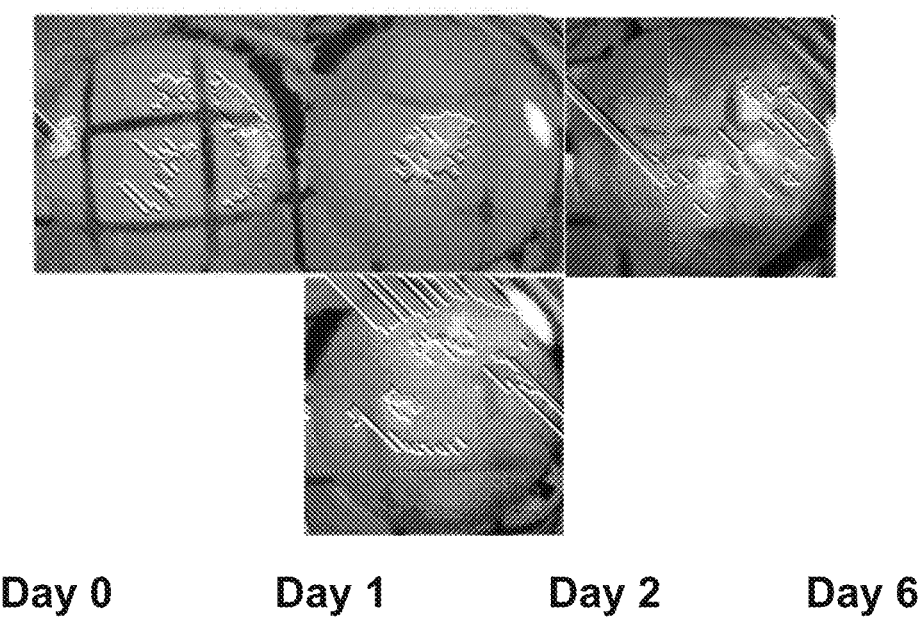
FIG. 10 is a series of images of freshly-isolated porcine lenses showing the opacification of the lenses upon culturing the lenses for a time period.

To analyze the efficacy and the biocompatibility of the compositions produced as described above, an ex viva analysis was undertaken in which the compositions were applied to eye lenses ex vivo. In these experiments, harvested porcine lenses were utilized. However, because freshly (less than 6 hrs) harvested porcine lenses typically opacify within 48 hours of being cultured in HEPES buffer ex vivo (see, e.g., FIG. 10), a revised lens culture method was developed to clear the lenses and allow them to be used to assess the clarity and other properties of the compositions. Briefly, in these experiments, it was found that M199 culture medium (Gibcol@ #11043-023, without Phenol red, Invitrogen, Carlsbad, CA) supplemented with 4% sterile-filtered porcine serum, 100 units/ml penicillin and 100 μg/ml streptomycin, and additional 5.96 g/L HEPES was preferable. In that modified medium, the lenses initially became opaque, but subsequently cleared up within 7 to 10 days under normoxic conditions. After this period, the lenses remained clear and could be used for experiments.

Figure 11:
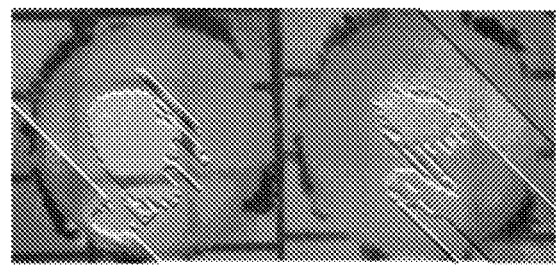
FIG. 11 is a pair of images showing the formation of a cataract in a porcine lens subsequent to culturing the lens with 1 mM $H_2O_2$ over a time period.
Figure 12:
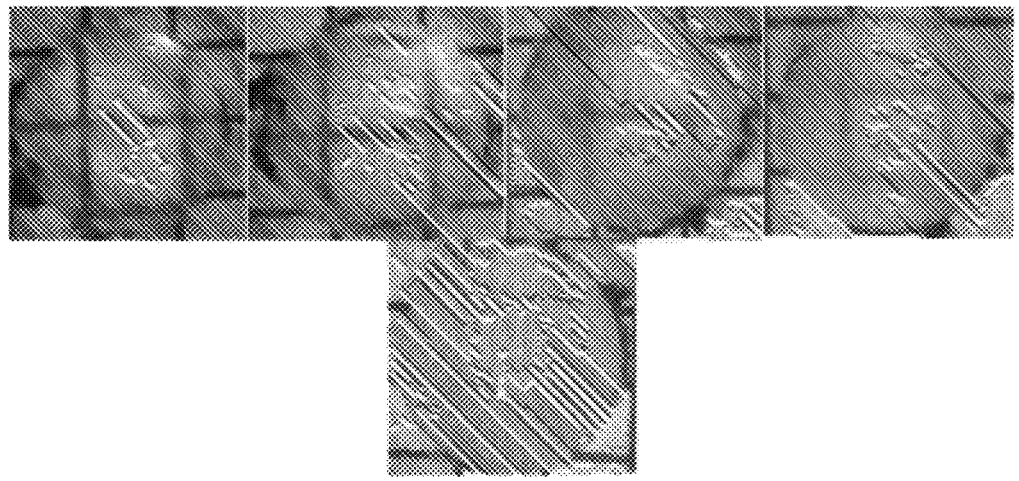
FIG. 12 is a series of lenses showing the formation of a cataract in a porcine lens subsequent to culturing the lens with 0.5 mM $H_2O_2$ over a time period.

Upon establishing the culturing conditions for the lenses, hyperoxic conditions were created and used to test the efficacy of the gelled compositions in protecting against oxidative damage and cataract formation. Briefly, in these experiments, two methods were used to test the efficacy of the compositions in preventing oxidative lens damage. Initially, oxidative damage with superoxide radicals generated by the addition of hydrogen peroxide into the lens culture medium was employed. In those initial experiments, initiation of the cataract and the extent of the cataract was found to be dependent on the concentration of $H_2O_2$. In particular, with 1 mM $H_2O_2$ lens opacity first appeared at 24 hr and turned into a total cataract by day 5 (FIG. 11), whereas with 0.5 mM $H_2O_2$, lens opacity started at day 3 and reached to 90% on day 14 (FIG. 12), and whereas with 0.4 mM $H_2O_2$, lens opacity started on day 5 and covered 60% of the lens area by day 14. As a result of these experiments, the preferred concentration for the experiments was found to be 0.3 mM of $H_2O_2$ which started to affect lens clarity on day 9 and caused 40% of the lens area to undergo opacification by day 14. $H_2O_2$ concentrations below 0.3 mM did not appear to cause any lens opacification for up to 28 days of ex vivo culturing. Of course, because the direct bathing of the lenses with $H_2O_2$ generated super-pharmacological amounts of free oxygen radicals that resulted in lens opacification within days, unlike in human conditions where cataract formation takes years, each of the foregoing experiments were conducted in a closed chamber that allowed ambient oxygen amounts to be tuned in fine increments and allowed lenses to be continuously bathed with oxygenated medium, with the dissolved oxygen being continuously monitored with an oxymeter.

Figure 13:
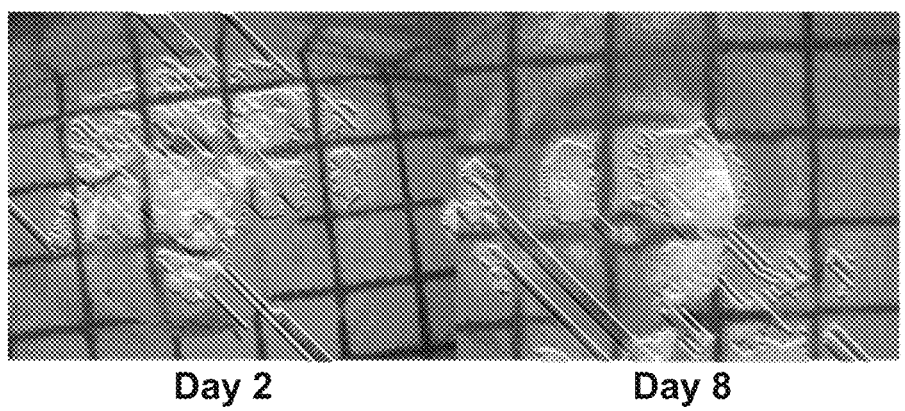
FIG. 13 is a pair of images showing the effect of coating a porcine lens with a polymeric composition of the presently-disclosed subject matter, where the composition failed to cause an opacity in the lens over a time period.

Once the parameters for exposing porcine lenses to hyperoxic conditions were established, before exposing lenses coated with the compositions described herein to hyperoxic conditions, the effect of coating the lenses with the compositions under normoxic conditions was first assessed. In these experiments, the unpolymerized compositions were placed on the lenses, photopolymerized, and then clarity of the lenses was assessed over a period of 8 days by comparing the coated lenses to uncoated control lenses. Throughout the course of the experiment, it was observed that the composition (i.e., the lens coating) did not cause any opacity in cultured porcine lenses (FIG. 13), nor did it affect does not affect lens epithelial cell viability.

Figure 14:
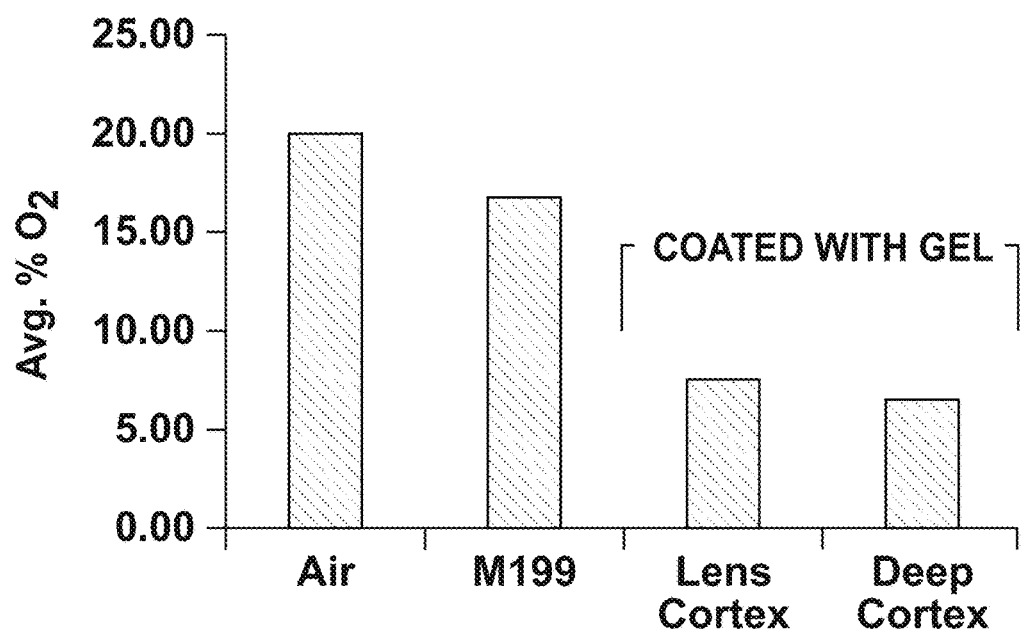
FIG. 14 is a graph showing the effect of coating a porcine lens with a polymeric composition of the presently-disclosed subject matter on oxygen diffusion into the lens.

To determine the effect of coating the lenses with the composition on oxygen diffusion, oxygen levels in air and M199 media were measured with a FireSting Oxygen Probe (PyroScience, Aachen, Germany), followed by measuring the oxygen levels at the lens cortex of a lens coated with 1 mm of the compositions described herein and in the deep cortex of the lens. Probe position was confirmed using a dissecting microscope with digital camera. Using a FireSting Oxymeter, it was observed that coating the compositions with the lenses resulted in an approximately 4 fold decrease in then amount of oxygen diffusing into the lens (FIG. 14).

Figure 15:
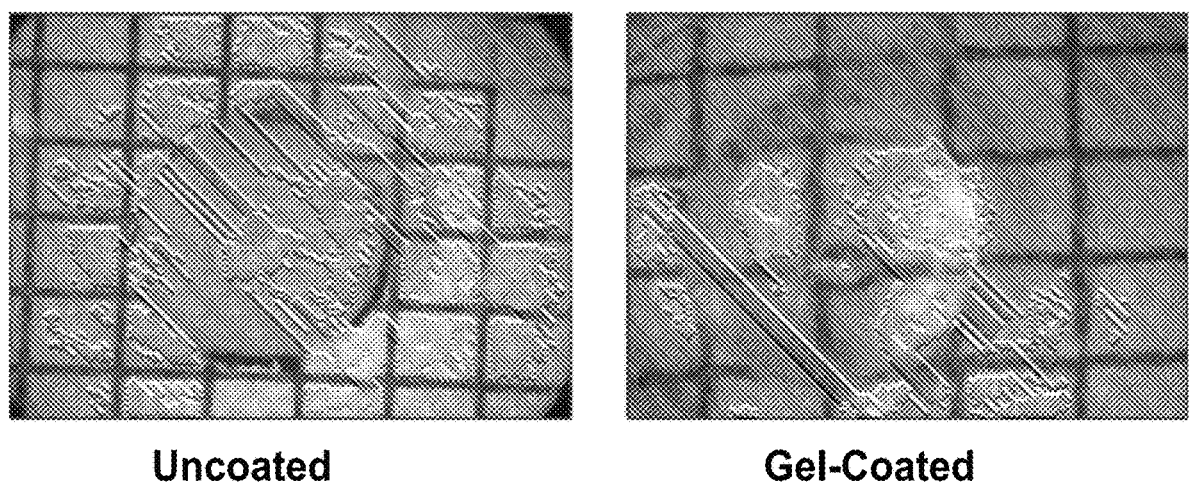
FIG. 15 is a pair of images showing a reduction in opacification of a porcine lens coated with a polymeric composition of the presently-disclosed subject matter relative to an uncoated lens, where each lens was cultured with 0.3 mM $H_2O_2$.

Lenses were then coated with the compositions and exposed to hyperoxic conditions (0.3 mM of $H_2O_2$). Opacification of the coated lens was prevented over the course of the experiment (FIG. 15).

REFERENCES

Throughout this document, various references are mentioned. All such references, including those listed below, are incorporated herein by reference.

1. Buerk, D. G., R. D. Shonat, C. E. Riva, and S. D. Cranstoun, O2 Gradients and Countercurrent Exchange in the Cat Vitreous Humor near Retinal Arterioles and Venules. Microvasc Res, 45(2): p.134-48, 1993.
2. Shui, Y. B., J. J. Fu, C. Garcia, L. K. Dattilo, R. Rajagopal, S. Mcmillan, G. Mak, N. M. Holekamp, A. Lewis, and D. C. Beebe, *Oxygen Distribution in the Rabbit Eye and Oxygen Consumption by the Lens.* Invest Ophthalmol Vis Sci, 47(4): p.1571-80, 2006.
3. Stefansson, E., *Physiology of Vitreous Surgery.* Graefes Arch Clin Exp Ophthalmol, 247(2): p.147-63, 2009.
4. Barbazetto, I. A., J. Liang, S. Chang, L. Zheng, A. Spector, and J. P. Dillon, *Oxygen Tension in the Rabbit Lens and Vitreous before and after Vitrectomy.* Exp Eye Res, 78(5): p.917-24, 2004.
5. Beebe, D. C., N. M. Holekamp, C. Siegfried, and Y. B. Shui, *Vitreoretinal Influences on Lens Function and Cataract.* Philos Trans R Soc Lond B Biol Sci, 366(1568): p.1293-300, 2011.
6. Holekamp, N M., Y. B. Shui, and D. C. Beebe, Vitrectomy Surgery Increases Oxygen Exposure to the Lens: A Possible Mechanism for Nuclear Cataract Formation. Am J Ophthalmol, 139(2): p.302-10, 2005.
7. Beebe, D. C., N. M. Holekamp, and Y. B. Shui, *Oxidative Damage and the Prevention of Age-Related Cataracts.* Ophthalmic Res, 44(3): p.155-65, 2010.
8. Schwartz, D. M., K. G. Duncan, and J. M. Stewart, Biodegradable Peg Based Polymer Formulations in Ocular Applications, US 2003/0223957 A110/410,860, 2003
9. Dillon, J., Methods and Compositions for Protecting against Cataract Development Associated with Vitrectomies, WO 2005/0489202005
10. Matier, W. L. and G. Patil, Amelioration of Vitrectomy-Induced Cataracts, U.S. Pat. No. 7,589,107 B211/439, 404, 2009
11. Liesegang, T. J., *Viscoelatic Substances in Ophthalmology.* Survey of ophthalmology, 34(4): p.268-93, 1990.
12. Hillel, A. T., S. Unterman, Z. Nahas, B. Reid, J. M. Coburn, J. Axelman, J. J. Chae, Q. Guo, R. Trow, A. Thomas, Z. Hou, S. Lichtsteiner, D. Sutton, C. Matheson, P. Walker, N. David, S. Mori, J. M. Taube, and J. H. Elisseeff, *Photoactivated Composite Biomaterial for Soft Tissue Restoration in Rodents and in Humans.* Science translational medicine, 3(93): p.93ra67, 2011.
13. Mann, B. K., A. S. Gobin, A. T. Tsai, R. H. Schmedlen, and J. L. West, Smooth Muscle Cell Growth in Photopolymerized Hydrogels with Cell Adhesive and Proteolytically Degradable Domains: Synthetic Ecm Analogs for Tissue Engineering. Biomaterials, 22(22): p.3045-51, 2001.
14. Porter, A. M., C. M. Klinge, and A. S. Gobin, *Biomimetic Hydrogels with VEGF Induce Angiogenic Processes in Both Huvec and Hmec.* Biomacromolecules, 12(1): p.242-6, 2011.
15. Wang, Y. X., J. L. Robertson, W. B. Spillman, and R. O. Claus, *Effects of the Chemical Structure and the Surface Properties of Polymeric Biomaterials on their Biocompatibility.* Pharmaceutical Research, 21(8): p.1362-1373, 2004.
16. Yasui, T., M. R. Mohamadi, N. Kaji, Y. Okamoto, M. Tokeshi, and Y. Baba, Characterization of Low Viscosity Polymer Solutions for Microchip Electrophoresis of Non-Denatured Proteins on Plastic Chips. Biomicrofluidics, 5(4), 2011.
17. Shin, S. C., J. W. Lee, K. H. Yang, and C. H. Lee, *Preparation and Evaluation of Bioadhesive Benzocaine Gels for Enhanced Local Anesthetic Effects.* International journal of pharmaceutics, 260(1): p.77-81, 2003.
18. Hill-West, J. L., S. M Chowdhury, M. J. Slepian, and J. A. Hubbell, *Inhibition of Thrombosis and intimal Thickening by in Situ Photopolymerization of Thin Hydrogel Barriers.* Proceedings of the National Academy of Sciences of the United States of America, 91(13): p.5967-71, 1994.
19. Buwalda, S. J., L. B. Perez, S. Teixeira, L. Calucci, C. Forte, J. Feijen, and P. J. Dijkstra, *Self-Assembly and*

*Photo-Cross-Linking of Eight-Armed Peg-Ptmc Star Block Copolymers.* Biomacromolecules, 12(7): p.2746-54, 2011.
20. Williams, C. G., A. N Malik, T. K. Kim, P. N. Manson, and J. H. Elisseeff, Variable Cytocompatibility of Six Cell Lines with Photoinitiators Used for Polymerizing Hydrogels and Cell Encapsulation. Biomaterials, 26(11): p.1211-8, 2005.
21. Ayranci, E. and S. Tunc, A Method for the Measurement of the Oxygen Permeability and the Development of Edible Films to Reduce the Rate of Oxidative Reactions in Fresh Foods. Food Chemistry, 80(3): p.423-431, 2003.
22. Sabnis, A., M. Rahimi, C. Chapman, and K. T. Nguyen, Cytocompatibility Studies of an in Situ Photopolymerized Thermoresponsive Hydrogel Nanoparticle System Using Human Aortic Smooth Muscle Cells. Journal of biomedical materials research. Part A, 91(1): p.52-9, 2009.
23. De Moura, M. R., R. J. Avena-Bustillos, T. H. Mchugh, J. M. Krochta, and L. H. Mattoso, *Properties of Novel Hydroxypropyl Methylcellulose Films Containing Chitosan Nanoparticles.* Journal of food science, 73(7): p.N31-7, 2008.
24. Ouasti, S., R. Donno, F. Cellesi, M. J. Sherratt, G. Terenghi, and N. Tirelli, *Network Connectivity, Mechanical Properties and Cell Adhesion for Hyaluronic Acid/Peg Hydrogels.* Biomaterials, 32(27): p.6456-70, 2011.
25. Park, Y. D., N. Tirelli, and J. A. Hubbell, *Photopolymerized Hyaluronic Acid-Based Hydrogels and Interpenetrating Networks.* Biomaterials, 24(6): p.893-900, 2003.
26. Pekel, N., Radiation Crosslinking of Biodegradable Hydroxypropylmethylcellulose. Carbohydrate Polymers, 55(2): p.139-147, 2004.
27. Charles, P. T., V. R. Stubbs, C. M. Soto, B. D. Martin, B J. White, and C. R. Taitt, Reduction of Non-Specific Protein Adsorption Using Poly(Ethylene)Glycol (Peg) Modified Polyacrylate Hydrogels in Immunoassays for Staphylococcal Enterotoxin B Detection. Sensors, 9(1): p.645-55, 2009.
28. Geraldine, P., B. B. Sneha, R. Elanchezhian, E. Ramesh, C. M. Kalavathy, J. Kaliamurthy, and P. A. Thomas, *Prevention of Selenite-Induced Cataractogenesis by Acetyl-L-Carnitine: An Experimental Study.* Exp Eye Res, 83(6): p.1340-9, 2006.
29. Piper, D. J., *Cataract Prevention Material,* in *Go/NoGO Assessment Report.* 2012, Foresight Science and Technology: Providence, RI.
30. Webb, B. C., Synthetic Viscoeleastic Material for Ophthalmic Applications, U.S. RE4224308/870,199, 2011
31. Tsuzuki, A., S. Iwamuro, and S. Tanikawa, Ophthalmic Solution, US 2006/0052340 A1, 2006
32. Kleinberg, T. T., R. T. Tzekov, L. Stein, N. Ravi, and S. Kaushal, *Vitreous Substitutes: A Comprehensive Review.* Surv Ophthalmol, 56(4): p.300-23, 2011.
33. Lin, S., N. Sangaj, T. Razafiarison, C. Zhang, S. Vargese, *Influence of physical properties of biomaterials on cellular behavior.* Pharm Res., 28(6): 1422-30, 2011.
34. Johnson, L. M., C. A. Deforest, A. Pendurti, K. S. Anseth, C. N. Bowman, *Formation of three-dimensional hydrogel multilayers using enzyme-mediated redox chain reaction initiation.* ACS Appl Mater Interfaces, 2(7): 1963-72, 2010.

What is claimed is:

1. A method comprising contacting an eye lens of a subject during vitrectomy with a composition comprising trehalose in an amount sufficient to reduce or prevent oxidative damage to the eye lens.
2. The method according to claim 1, wherein contacting the eye lens of the subject comprises coating the eye lens with the composition.
3. The method according to claim 1, wherein the composition is contacted with the eye lens in an amount sufficient to prevent post-vitrectomy cataract formation.
4. The method according to claim 1, wherein the composition has a surface energy of less than about 4 dyne/cm or greater than about 40 dyne/cm.
5. The method according to claim 4, wherein the composition has an elasticity of about 50 N/m to about 1000 N/m.
6. The method according to claim 5, wherein the composition has an osmolarity of about 281 mOsm to about 350 mOsm.
7. The method according to claim 1, wherein the composition further comprises one or more of an emulsifier and a nonionic surfactant.
8. The method according to claim 1, wherein the composition further comprises one or more of a poly (ethylene glycol) and a viscoelastic polymer.
9. The method according to claim 8, further comprising polymerizing the composition.
10. The method according to claim 8, wherein the poly (ethylene glycol) is poly(ethylene glycol) diacrylate.
11. The method according to claim 8, wherein the viscoelastic polymer is selected from the group consisting of hyaluronic acid or a salt thereof, hydroxymethylpropyl cellulose, chondroitin sulfate, polyacrylamide, collagen, dextran, heparin, agarose, chitosan, and combinations thereof.
12. The method according to claim 8, wherein the composition further comprises a photoinitiator.
13. The method according to claim 12, wherein the photoinitiator is selected from the group consisting of 2-hydroxy-4'-(2-hydroxyethoxy)-2-methylpropiophenone, eosin Y, triethanolamine, 1-vinyl-2-pyrrolidinone, and combinations thereof.
14. A composition comprising trehalose in an amount sufficient to reduce or prevent oxidative damage when applied to the eye lens during vitrectomy.

* * * * *